United States Patent
Floro et al.

(10) Patent No.: US 10,111,438 B2
(45) Date of Patent: *Oct. 30, 2018

(54) COMPOSITIONS AND METHODS FOR IMPROVING FRUIT PRODUCTION

(71) Applicant: NewLeaf Symbiotics, Inc., St. Louis, MO (US)

(72) Inventors: Rachel DiDonato Floro, St. Louis, MO (US); Justin Lee, St. Louis, MO (US); Gregg Bogosian, Clarkson Valley, MO (US)

(73) Assignee: NEWLEAF SYMBIOTICS, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/101,202

(22) PCT Filed: Dec. 4, 2014

(86) PCT No.: PCT/US2014/068663
§ 371 (c)(1),
(2) Date: Jun. 2, 2016

(87) PCT Pub. No.: WO2015/085117
PCT Pub. Date: Jun. 11, 2015

(65) Prior Publication Data
US 2016/0302424 A1    Oct. 20, 2016

Related U.S. Application Data

(60) Provisional application No. 61/911,577, filed on Dec. 4, 2013.

(51) Int. Cl.
*A01N 63/00* (2006.01)

(52) U.S. Cl.
CPC .................................. *A01N 63/00* (2013.01)

(58) Field of Classification Search
CPC ...................................................... A01N 63/00
USPC ....................................................... 504/117
See application file for complete search history.

(56) References Cited

U.S. PATENT DOCUMENTS

| | | |
|---|---|---|
| 2,200,532 A | 5/1940 | Bond et al. |
| 4,336,334 A | 6/1982 | Powell et al. |
| 5,013,665 A | 5/1991 | Suzuki et al. |
| 5,106,648 A | 4/1992 | Williams |
| 5,112,843 A | 5/1992 | Bjostad, III et al. |
| 5,302,525 A | 4/1994 | Groleau et al. |
| 5,344,768 A | 9/1994 | Urakami |
| 5,403,799 A | 4/1995 | Miller et al. |
| 5,403,809 A | 4/1995 | Miller et al. |
| 5,512,069 A | 4/1996 | Holland et al. |
| 5,686,276 A | 11/1997 | Laffend et al. |
| 5,961,687 A | 10/1999 | Joshi et al. |
| 6,107,067 A | 8/2000 | Miller et al. |
| 6,174,837 B1 | 1/2001 | Joshi et al. |
| 6,329,320 B1 | 12/2001 | Joshi et al. |
| 7,214,509 B2 | 5/2007 | Schnoor et al. |
| 7,435,878 B2 | 10/2008 | Holland |
| 8,153,118 B2 | 4/2012 | Holland et al. |
| 8,181,388 B2 | 5/2012 | Berger |
| 8,778,660 B2 | 7/2014 | Holland et al. |
| 9,181,541 B2 | 11/2015 | Bogosian |
| 2001/0001095 A1 | 5/2001 | Joshi et al. |
| 2003/0211082 A1 | 11/2003 | Holland |
| 2005/0096225 A1 | 5/2005 | Johnson |
| 2006/0059581 A1 | 3/2006 | Spencer et al. |
| 2006/0150488 A1 | 7/2006 | Pearce et al. |
| 2006/0166346 A1 | 7/2006 | Takagi et al. |
| 2006/0228797 A1 | 10/2006 | Holland et al. |
| 2007/0074451 A1 | 4/2007 | Pearce et al. |
| 2007/0265166 A1 | 11/2007 | Bardella et al. |
| 2010/0093538 A1 | 4/2010 | Gnanamanickam |
| 2011/0269219 A1 | 11/2011 | Holland et al. |
| 2013/0324407 A1 | 12/2013 | Bogosian |
| 2015/0337256 A1 | 11/2015 | Bogosian |
| 2016/0046925 A1 | 2/2016 | Bogosian |
| 2016/0073641 A1 | 3/2016 | Allen et al. |
| 2016/0120188 A1 | 5/2016 | Bogosian |
| 2016/0295868 A1 | 10/2016 | Jones et al. |
| 2016/0302423 A1 | 10/2016 | Jones et al. |

(Continued)

FOREIGN PATENT DOCUMENTS

| | | |
|---|---|---|
| CA | 2183275 A1 | 2/1998 |
| CN | 101028008 A | 9/2007 |

(Continued)

OTHER PUBLICATIONS

ATCC Catalogue. ATCC Bacteria and Bacteriophages, 19th edition, 1996, pp. 231-214.*
ATCC Preservation Methods: Freezing and freeze-drying; Published by ATCC, 2nd edition, 1991, pp. 5-13.*
Wessman et al. (J. Sci Food Agric 2011,91, pp. 2518-2528.*
Franzetti et al., "Phylogenetic Characterization of Bioemulsifier-Producing Bacteria", International Biodeterioration & Biodegradation, Aug. 19, 2011, pp. 1095-1099, vol. 65 (entire document).
International Search Report and Written Opinion dated Feb. 23, 2015, issued in PCT Patent Application No. PCT/US2014/068663.

(Continued)

*Primary Examiner* — Johann R Richter
*Assistant Examiner* — Courtney A Brown
(74) *Attorney, Agent, or Firm* — Thompson Coburn LLP; Charles P. Romano

(57) ABSTRACT

The present invention provides compositions comprising *Methylobacterium* and depleted of substances that promote growth of resident microorganisms on a plant or seed, methods for improving fruit production, methods of making the compositions, and methods of treating a plant or seed with a composition comprising *Methylobacterium*. Also provided are methods and compositions comprising *Methylobacterium* that provide for improved fruit production.

16 Claims, No Drawings

(56) References Cited

U.S. PATENT DOCUMENTS

| | | | |
|---|---|---|---|
| 2016/0302425 | A1 | 10/2016 | DiDonato et al. |
| 2017/0086464 | A1 | 3/2017 | Floro et al. |
| 2017/0135352 | A1 | 5/2017 | Breakfield et al. |
| 2017/0164618 | A1 | 6/2017 | Breakfield et al. |
| 2017/0238553 | A1 | 8/2017 | Jones et al. |

FOREIGN PATENT DOCUMENTS

| | | | | |
|---|---|---|---|---|
| EP | 0140723 | A1 | 5/1985 | |
| EP | 2390345 | A1 | 11/2011 | |
| KR | 100755509 | B1 | 9/2007 | |
| KR | 20070106867 | A | 11/2007 | |
| KR | 20070106868 | A | 11/2007 | |
| KR | 20070111915 | A | 11/2007 | |
| KR | 20080097568 | A | 11/2008 | |
| KR | 100953179 | B1 | 4/2010 | |
| KR | 10-1195899 | B1 | 10/2012 | |
| WO | 9943632 | A1 | 9/1999 | |
| WO | WO-9943632 | A1 * | 9/1999 | ............ A01C 1/00 |
| WO | 2003046226 | A1 | 6/2003 | |
| WO | 2012012671 | A2 | 1/2012 | |
| WO | 2012140207 | A2 | 10/2012 | |
| WO | 2012140212 | A2 | 10/2012 | |
| WO | WO 2012140212 | A2 * | 10/2012 | ............ A01N 63/00 |
| WO | WO 2013090628 | A1 * | 6/2013 | ............ A01N 63/00 |
| WO | 2013141815 | A1 | 9/2013 | |
| WO | WO 2013141815 | A1 * | 9/2013 | ............ A01N 63/00 |
| WO | 2013181610 | A1 | 12/2013 | |
| WO | 2015085115 | A1 | 6/2015 | |
| WO | 2015142393 | A1 | 9/2015 | |
| WO | 2016069564 | A1 | 5/2016 | |
| WO | 2016201284 | A2 | 12/2016 | |

OTHER PUBLICATIONS

Joe et al., "Development of Alginate-Based Aggregate Inoculants of *Methylobacterium* sp. and Azospirillum brasilense Tested under in Vitro Conditions to Promote Plant Growth", Journal of Applied Biology, Nov. 4, 2013, pp. 408-423, vol. 116 (entire document).

Kailasapthy et al., "Microencapsulation of Probiotic Bacteria: Technology and Potential Applications", Current Issues of Intestinal Microbiology, Sep. 1, 2002, pp. 39-48, vol. 3 (entire document).

SY, A. et al., "Methylotrophic Metabolism Is Advantageous for Methylobacterium extorquens during Colonization of Medicago truncatula under Competitive Conditions", Applied and Environmental Microbiology, 2005, pp. 7245-7252, vol. 71, No. 11.

"NewLeaf Symbiotics Strain Isolate Record", dated Nov. 6, 2017.

Abanda-Nkpwatt et al., "Molecular Interaction Between Methylobacterium Extorquens and Seedlings: Growth Promotion, Methanol Consumption, and Localization of the Methanol Emission Site", Journal of Experimental Botany, Oct. 16, 2006, pp. 4025-4032, vol. 57 No. 15.

Balachandar et al., "Genetic and Metabolic Diversity of Pink-Pigmented Facultative Methylotrophs in Phyllosphere of Tropical Plants", Brazilian Journal of Microbiology, 2008, pp. 68-73, vol. 39.

Bardi et al., "Immobilization of Yeast on Delignified Cellulosic Material for Low Temperature Brewing", Journal of Agricultural and Food Chemistry, 1996, pp. 463-467, vol. 44 No. 2.

Chitra et al., "Multigeneric PGPR Coaggregates: A Novel Bioformulation and Delivery System for the Induction of Systemic Resistance in Rice-Xanthomonas Oryzae Pathosystem Under Lowland Condition", Golden Research Thoughts, Oct. 2013, pp. 1-10, vol. 3, No. 4.

Chitra et al.,"Multigeneric Microbial Coaggregates-Effect of Different Bioformulations of PGPR Cells on the Enhancement of PGPR Characteristics and Biocontrol Against Xanthomonas oryzae pv. oryzae in Rice Grown Under Lowland Condition", Journal of Applicable Chemistry, 2013, pp. 1132-1140, vol. 2, No. 5.

Corpe et al., "Ecology of the Methylotrophic Bacteria on Living Leaf Surfaces", FEMS Microbiology Ecology, 1989, pp. 243-250, vol. 62.

Corpe et al., "Methanol-Utilizing Bacteria Associated with Green Plants", Developments in Industrial Microbiology, 1982, pp. 483-493, vol. 23.

De Valdez et al., "Effect of Drying Medium on Residual Moisture Content and Viability of Freeze-Dried Lactic Acid Bacteria", Applied and Environmental Microbiology, Feb. 1985, pp. 413-415, vol. 49, No. 2.

GenBank entry FP103042, Nov. 5, 2010, retreived on Jan. 5, 2016 from http://www.ncbi.nlm.nih.gov/nuccore/254265931?sat=18&satkey-27964264.

Gomathy et al., "Impact of Biofertigation of Azophosmet on Cotton Yield under Dripirrigation", Research Journal of Agriculture and Biological Sciences, 2008, pp. 695-699, vol. 4, No. 6.

Green, "Methylobacterium", In: Prokaryotes, 2006, pp. 257-265, vol. 5.

Holland, "Methylobacterium and Plants", Recent Research Developments in Plant Physiology, 1997, pp. 207-213, vol. 1.

http://www.bacterio.net/methylobacterium.html, downloaded on Oct. 12, 2017, 12 pages.

International Search Report and Written Opinion dated Apr. 28, 2015, issued in PCT Patent Application No. PCT/US2014/068558.

International Search Report and Written Opinion dated Feb. 16, 2016, issued in PCT Patent Application No. PCT/US2015/057521.

International Search Report and Written Opinion dated Feb. 20, 2015, issued in PCT Patent Application No. PCT/US2014/068657.

International Search Report and Written Opinion dated Mar. 2, 2015, issued in PCT Patent Application No. PCT/US2014/068660.

International Search Report and Written Opinion for PCT/US2013/043722 dated Aug. 23, 2013.

Jiang et al., "Methanotrophs: Multifunctional Bacteria with Promising Applications in Environmental Bioengineering", Biochemical Engineering Journal, May 15, 2010, pp. 277-288, vol. 49 No. 3.

Joe et al., Development of Alginate-Based Aggregate Inoculants of *Methylobacterium* sp. and Azospirillum brasilense Tested Under in vitro Conditions to Promote Plant Growth, Journal of Applied Microbiology, Nov. 2012, pp. 1-46.

Kongkhaem et al., "Silica-Immobilized *Methylobacterium* sp. NP3 and *Acinetobacter* sp. PK1 Degrade High Concentrations of Phenol", Letters in Applied Microbiology, May 2011, pp. 448-455, vol. 52 No. 5.

Leslie et al., "Trehalose and Sucrose Protect Both Membranes and Proteins in Intact Bacteria during Drying", Applied and Environmental Microbiology, Oct. 1995, pp. 3592-3597, vol. 61 No. 10.

Li et al., "2,4,5,-Trichlorophenol Degradation Using a Novel TiO2-Coated Biofilm Carrier: Roles of Adsorption, Photocatalysis, and Biodegradation", Environmental Science & Technology, Aug. 23, 2011, pp. 8359-8367 vol. 45. No. 19.

Lidstrom et al., "Plants in the Pink: Cytokinin Production by Methylbacterium", Journal of Bacteriology, Apr. 2002, p. 1818, vol. 184, No. 7.

Madhaiyan et al., "Growth Promotion and Induction of Systemic Resistance in Rice Cultivar Co-47 (*Oryza sativa* L.) by *Methylobacterium* spp.", Botanical Bulletin of the Academia Sinica, 2004, pp. 315-324, vol. 45.

Madhaiyan et al., "Metal Tolerating Methylotrophic Bacteria Reduces Nickel and Cadmium Toxicity and Promotes Plant Growth of Tomato (*Lycopersicon esculentum* L.)", Chemosphere, May 23, 2007, pp. 220-228, vol. 69.

Madhaiyan et al., "Pink-Pigmented Facultative Methylotrophic Bacteria Accelerate Germination, Growth and Yield of Sugarcane Clone Co86032 (*Saccharum officinarum* L.)", Biology of Fertile Soils, 2005, pp. 350-358, vol. 41.

Ntsaluba et al., "Studies on Bioflocculant Production by *Methylobacterium* sp. Obi Isolated from a Freshwater Environment in South Africa", African Journal of Microbiology Research, Nov. 16, 2011, pp. 4533-4540, vol. 5 No. 26.

Omer et al., "Plant Colonization by Pink-Pigmented Facultative Methylotrophic Bacteria (PPFMs)", FEMS Microbiology Ecology, Mar. 2004, pp. 319-326, vol. 47 No. 3.

Pacific Ag Research, "Evaluation of Efficacy Using NLS Strains as Biostimulant in Direct Seeded Cool Season Lettuce Approach", Research and Development Project Report, Winter-Summer 2015.

(56) References Cited

OTHER PUBLICATIONS

Poorniammal et al., "In Vitro Biocontrol Activity of Methylobacterium Extorquens Against Fungal Pathogens", International Journal of Plant Protection, 2009, pp. 59-62, vol. 2, No. 1.

Ransom et al., "Corn Growth and Mangement: Quick Guide", North Dakota State University, May 1, 2013, pp. 1-8, Retrieved from www.ag.ndsu.edu/pubs/plantsci/crops/a1173.pdf, on Feb. 4, 2015, entire document.

Rastogi et al., "Leaf Microbiota in an Agroecosystem Spatiotemporal Variation in Bacterial Community Composition on Field-Grown Lettuce", The ISME Journal, Apr. 26, 2012. pp. 1812-1822, vol. 6.

RD4AG Lettuce Field Trial Report dated Jan. 30, 2015.

RD4AG Lettuce Field Trial Report dated May 31, 2015.

Ryu et al., "Plant Growth Substances Produced by *Methylobacterium* spp. and Their Effect on Tomato (*Lycopersicon esculentum* L.) and Red Pepper (*Capsicum annuum* L) Growth", Journal of Microbiology and Biotechnology, Oct. 2006, pp. 1622-1628, vol. 16, No. 10.

Simoes et al., "Adhesion and Biofilm Formation on Polystyrene by Drinking Water-Isolated Bacteria", Antonie van Leeuwenhoek, Apr. 20, 2010, pp. 317-329, vol. 98 No. 3.

Sundaram et al., "Bioinoculants for Sustainable and Cost Effective Production of High Quality Fibre", TMC Annual Report, TMC-MMI-2.3, 2006, pp. 1-7, Retrieved from the internet, Apr. 2, 2014, http://www.tmc.cicr.org.in/PDF/22.3.pdf.

Tani et al, "Methylobacterium Species Promoting Rice and Barley Growth and Interaction Specificity Revealed with Whole-Cell Matrix-Assisted Laser Desorption / Ionization-Time-of-Flight Mass Spectrometry (MALDI-TOF/MS) Analysis", PLOS One, Jun. 8, 2015, 15 pages.

Vaidehi et al., "Adhesion of Methylobacterium Cells to Rice Roots: Active Metabolism of Miropartner Determines the Degree of Adsorption Level at Rhizosphere", International Journal of Research in Pure and Applied Microbiology, 2012, pp. 54-58, vol. 2, No. 4.

Verhoef et al., "*Methylobacterium* sp. Isolated from a Finnish Paper Machine Produces Highly Pyruvated Galactan Exopolysaccharide", Carbohydrate Research, 2003, pp. 1851-1859, vol. 338.

Vuilleumier et al., "Methylobacterium Genome Sequences: A Reference Blueprint to Investigate Microbial Metabolism of C1 Compounds from Natural and Industrial Sources", Public Library of Science One, May 18, 2009, pp. 1-16; vol. 4, No. 5.

Lee et al., "Foliar Colonization and Growth Promotion of Red Pepper (*Capsicum annuum* L.) by Methylobacterium oxyzae CBMB20", Journal of Applied Biologiacal Chemistry, 2011, pp. 120-125, vol. 54, No. 2.

Prabhu et al, "Suppressive Effect of Methylobacterium fujisawaense Against Root-Knot Nematode, Meloidogyne Incognita", Indian Journal of Nematology, 2009, pp. 165-169, vol. 39, No. 2.

Vetrivelkalai et al., "Biocontrol Potential of Endophytic Bacteria on Meloidogyne Incognita and its Effect on Plant Growth in Blendhi", Journal of Biopesticides, 2010, pp. 452-457, vol. 3, No. 2.

* cited by examiner

COMPOSITIONS AND METHODS FOR IMPROVING FRUIT PRODUCTION

CROSS REFERENCE TO RELATED APPLICATIONS

This patent application is a 35 U.S.C. 371 US national stage application of International patent application PCT/US2014/068663, filed Dec. 4, 2014 and incorporated herein by reference in its entirety, which claims the benefit of U.S. Provisional Patent Application No. 61/911,577, filed Dec. 4, 2013, which is incorporated herein by reference.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum*, and *Methylocella* (Lidstrom, 2006). Methanotrophs possess the enzyme methane monooxygenase, that incorporates an atom of oxygen from $O_2$ into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

SUMMARY

Provided herein are compositions comprising *Methylobacterium* that are depleted of substances that promote growth of resident bacteria on the plant or seed, compositions comprising a solid substance with adherent *Methylobacterium* grown thereon or an emulsion having *Methylobacterium* grown therein, compositions comprising certain *Methylobacterium* strains and derivatives thereof and an agriculturally acceptable adjuvant and/or excipient, methods of using the compositions to improve fruit production, and methods of making the compositions. Such compositions are in certain instances referred to herein as simply "*Methylobacterium*-containing compositions". In certain embodiments, the *Methylobacterium* in the composition or that is used is strain NLS0038, NLS0046, NLS0020, NLS0017, NLS0042, NLS0089, NLS0068, NLS0065, NLS0069, NLS0062, NLS0064, NLS0021, NLS0066, or NLS0037. In certain embodiments, the *Methylobacterium* in the composition or that is used is strain NLS0037, NLS0042, or NLS0062. In certain embodiments, the *Methylobacterium* in the composition or that is used is strain NLS0037, NLS0042, or NLS0062. In certain embodiments of any of the foregoing embodiments, the composition further comprises an agriculturally acceptable adjuvant and/or excipient. Methods for improving fruit production are provided herein that comprise: (a) applying a composition comprising *Methylobacterium* to a fruit bearing plant or seed, which composition comprises: (i) a solid substance with adherent *Methylobacterium* grown thereon; (ii) an emulsion having *Methylobacterium* grown therein, or (iii) compositions comprising certain *Methylobacterium* strains and derivatives thereof; wherein the plant or plant grown from the seed exhibits faster fruit set, increased fruit set, earlier maturation, and/or more uniform fruit maturation compared to an untreated control plant, thereby obtaining improved fruit production. In certain embodiments, the methods further comprise (b) harvesting fruit from the plant or a plant grown from the seed. In certain embodiments of the methods, the composition comprises *Methylobacterium* at a titer of about $1\times10^6$ CFU/gm to about $1\times10^{14}$ CFU/gm for the solid-containing composition or at a titer of about $1\times10^6$ CFU/mL to about $1\times10^{11}$ CFU/mL for the emulsion-containing composition. In certain embodiments, the composition is depleted of substances that promote growth of resident bacteria on a plant or seed. In certain embodiments of the method, the fruit bearing plant is an apple, pear, grape, citrus, melon, pepper, tomato, berry, kiwi, mango, or banana plant. In certain embodiments, the berry plant is a blackberry, strawberry, or blueberry plant. In certain embodiments of the method, the applied composition coats or partially coats the plant, a part thereof, or the seed. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0037 (NRRL B-50941), NLS0038 (NRRL B-50942), NLS0042 (NRRL B-50932), NLS0062 (NRRL B-50937), and derivatives thereof. In certain embodiments, the *Methylobacterium* in the composition or that is used is selected from the group consisting of NLS0038 (NRRL B-50942), NLS0042 (NRRL B-50932), NLS0062 (NRRL B-50937), and derivatives thereof.

Also provided herein are methods for improving fruit production, the method comprising: (a) applying a composition comprising *Methylobacterium* to a fruit bearing plant or seed, wherein the composition comprises a *Methylobacterium* sp. selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069

(NRRL B-50936), NLS0089 (NRRL B-50933), and derivatives thereof and an agriculturally acceptable adjuvant, excipient, or combination thereof. In certain embodiments, the methods further comprise (b) harvesting fruit from the plant or a plant grown from the seed, wherein the plant or plant grown from the seed exhibits faster fruit set, increased fruit set, earlier maturation, and/or more uniform fruit maturation compared to an untreated control plant, thereby obtaining improved fruit production. In certain embodiments, the composition comprises *Methylobacterium* at a titer of about $1\times10^6$ colony-forming units per gram (CFU/gm) of solid to about $1\times10^{14}$ CFU/gm of solid for a composition comprising a solid substance with adherent *Methylobacterium* grown thereon or at a titer of about $1\times10^6$ CFU/mL to about $1\times10^{11}$ CFU/mL for a composition comprising an emulsion having *Methylobacterium* grown therein. In certain embodiments, the fruit bearing plant is an apple, pear, grape, citrus, melon, pepper, tomato, berry, kiwi, mango, or banana plant. In certain embodiments, the composition is depleted of substances that promote growth of resident microorganisms on the plant or seed. In certain embodiments, the *Methylobacterium* is selected from the group consisting of NLS0037 (NRRL B-50941), NLS0038 (NRRL B-50942), NLS0042 (NRRL B-50932), NLS0062 (NRRL B-50937), and derivatives thereof. In certain embodiments, the *Methylobacterium* is selected from the group consisting of NLS0038 (NRRL B-50942), NLS0042 (NRRL B-50932), NLS0062 (NRRL B-50937), and derivatives thereof. In certain embodiments, the composition coats or partially coats the plant or a part thereof, or the seed.

Also provided herein are methods for improving fruit production that comprise: (a) applying to a fruit bearing plant or seed a composition comprising *Methylobacterium* that is depleted of substances that promote growth of resident bacteria on said plant or seed, wherein the plant or plant grown from the seed exhibits faster fruit set, increased fruit set, earlier maturation, and/or more uniform fruit maturation compared to an untreated control plant, thereby obtaining improved fruit production. In certain embodiments, the methods further comprise (b) harvesting fruit from the plant or a plant grown from the seed. In certain embodiments of the method, the composition comprises a solid substance with adherent *Methylobacterium* grown thereon, wherein the *Methylobacterium* titer of about $1\times10^6$ CFU/gm to about $1\times10^{14}$ CFU/gm, or comprises a liquid, a solid substance with *Methylobacterium* adhered thereto in a liquid, a solid substance with *Methylobacterium* adhered thereto in an emulsion, or an emulsion having *Methylobacterium* grown therein at a titer of about $1\times10^6$ CFU/mL to about $1\times10^{11}$ CFU/mL. In certain embodiments of the method, the fruit bearing plant is an apple, pear, grape, citrus, melon, pepper, tomato, berry, kiwi, mango, or banana plant. In certain embodiments, the berry plant is a blackberry, strawberry, or blueberry plant. In certain embodiments of the method, the applied composition coats or partially coats the plant, a part thereof, or the seed. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0037 (NRRL B-50941), NLS0038 (NRRL B-50942), NLS0042 (NRRL B-50932), NLS0062 (NRRL B-50937), and derivatives thereof. In certain embodiments, the *Methylobacterium* is selected from the group consisting of NLS0038 (NRRL B-50942), NLS0042 (NRRL B-50932), NLS0062 (NRRL B-50937), and derivatives thereof.

Also provided herein are methods of preparing a plant or plant seed treatment composition that comprises *Methylobacterium* and is depleted of substances that promote growth of resident bacteria on a plant or seed. Such methods comprise (a) growing a mono-culture or co-culture of *Methylobacterium* in media that comprises: (i) an aqueous phase; (ii) a liquid phase and a solid phase; or (iii) an emulsion, thereby obtaining a *Methylobacterium*-containing media; (b) separating the *Methylobacterium* from at least one other portion of the *Methylobacterium*-containing media; and (c) reconstituting the *Methylobacterium* in a matrix lacking substances that promote growth of resident bacteria on a plant or seed. In certain embodiments, the separation step is effected by centrifugation, filtration, or settling of the *Methylobacterium*-containing media and removal of excess liquid or emulsion therefrom. In certain embodiments, the substance that promotes growth of resident bacteria on a plant or seed is selected from the group consisting of a carbon source, a nitrogen source, a phosphorous source, a sulfur source, a magnesium source, and combinations thereof. In certain embodiments, the matrix is a liquid, an emulsion, or one or more solids, and comprises an agriculturally acceptable adjuvant and/or excipient. In certain embodiments; the *Methylobacterium* are grown in media comprising a liquid phase and a solid substance with adherent *Methylobacterium* grown thereon, the solid substance is separated from the liquid phase of the *Methylobacterium*-containing media, and the solid substance with adherent *Methylobacterium* grown thereon is reconstituted in the aforementioned matrix. In certain embodiments, the solid substance with adherent *Methylobacterium* is not a substance that promotes growth of resident microorganisms on a plant, plant part, or plant seed. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0037 (NRRL B-50941), NLS0038 (NRRL B-50942), NLS0042 (NRRL B-50932), NLS0062 (NRRL B-50937), and derivatives thereof. In certain embodiments, the *Methylobacterium* is selected from the group consisting of NLS0038 (NRRL B-50942), NLS0042 (NRRL B-50932), NLS0062 (NRRL B-50937), and derivatives thereof.

A method of treating a plant or seed with a composition comprising *Methylobacterium* and depleted of substances that promote growth of resident bacteria on a plant or seed is provided herein. Such method comprises: (a) preparing a *Methylobacterium*-containing composition that is depleted of substances that promote growth of resident bacteria on a plant or seed according to any of the aforementioned methods; and, (b) applying the composition to a plant or seed. In certain embodiments of the methods, the composition is applied to the plant or a part thereof, or seed as a spray, or said composition is applied to said plant, plant thereof, or seed by immersion. In certain embodiments of the methods, the applied composition coats or partially coats the plant, the part thereof, or the seed. In certain embodiments of the methods, solid substance with adherent *Methylobacterium* is not a substance that promotes growth of resident microorganisms on a plant or seed. In certain embodiments of the methods, the composition comprises an agriculturally acceptable adjuvant and/or excipient. In certain embodiments of any of the aforementioned methods, the composition comprises a solid substance with adherent *Methylobacterium* grown thereon, wherein the *Methylobacterium* titer of about $1 \times 10^6$ CFU/gm to about $1 \times 10^{14}$ CFU/gm or comprises a liquid, a solid substance with *Methylobacterium* adhered thereto in a liquid, a solid substance with *Methylobacterium* adhered thereto in an emulsion, or an emulsion having *Methylobacterium* grown therein at a titer of about $1 \times 10^6$ CFU/mL to about $1 \times 10^{11}$ CFU/mL. Also provided are plant parts or plant seed that are coated or partially coated with a composition comprising *Methylobacterium* that is depleted of substances that promote growth of resident microorganisms on a plant or seed, wherein the plant parts or plant seed is obtained by any of the aforementioned methods. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0037 (NRRL B-50941), NLS0038 (NRRL B-50942), NLS0042 (NRRL B-50932), NLS0062 (NRRL B-50937), and derivatives thereof.

Methods of treating a plant or seed with *Methylobacterium* are provided herein. Such methods comprise applying to a plant or seed a composition comprising a solid substance with adherent *Methylobacterium* grown thereon and depleted of substances that promote growth of resident microorganisms on a plant or seed. In certain embodiments, the composition is applied to the plant or a part thereof as a spray, or the composition is applied to the plant, a part thereof, or seed by immersion. In certain embodiments, the applied composition coats or partially coats the plant, the part thereof, or the seed. In certain embodiments, the solid substance with adherent *Methylobacterium* is not a substance that promotes growth of resident microorganisms on a plant or seed. In certain embodiments, the composition comprises an agriculturally acceptable adjuvant and/or excipient. In certain embodiments of the methods, the applied composition coats or partially coats the plant, the part thereof, or the seed. In certain embodiments of the methods, solid substance with adherent *Methylobacterium* is not a substance that promotes growth of resident microorganisms on a plant or seed. In certain embodiments of any of the aforementioned methods, the composition comprises a solid substance with adherent *Methylobacterium* grown thereon, wherein the *Methylobacterium* titer of about $1 \times 10^6$ CFU/gm to about $1 \times 10^{14}$ CFU/gm or comprises a liquid, a solid substance with *Methylobacterium* adhered thereto in a liquid, a solid substance with *Methylobacterium* adhered thereto in an emulsion, or an emulsion having *Methylobacterium* grown therein at a titer of about $1 \times 10^6$ CFU/mL to about $1 \times 10^{11}$ CFU/mL. Also provided are plant parts or plant seed that are coated or partially coated with a composition comprising *Methylobacterium* that is depleted of substances that promote growth of resident microorganisms on a plant or seed, wherein the plant parts or plant seed is obtained by any of the aforementioned methods. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0037 (NRRL B-50941), NLS0038 (NRRL B-50942), NLS0042 (NRRL B-50932), NLS0062 (NRRL B-50937), and derivatives thereof.

Further provided herein is a composition comprising a solid substance with adherent *Methylobacterium* grown thereon, wherein the composition is depleted of substances that promote growth of resident microorganisms on a plant or seed. In certain embodiments, the adherent *Methylobacterium* are at a titer of at least about $1 \times 10^6$ CFU/gm to at least about $1 \times 10^{14}$ CFU/gm. In certain embodiments, the composition is a solid composition and the *Methylobacterium* are at a titer of about $1 \times 10^6$ CFU/gm to about $1 \times 10^{14}$ CFU/gm. In certain embodiments, the adherent *Methylobacterium* in the solid composition are at a titer of at least about $5 \times 10^8$ CFU/gm to at least about $5 \times 10^{13}$ CFU/gm. In certain embodiments, the composition is a liquid or an emulsion that contains the solid substance and the *Methylobacterium* are at a titer of about $1 \times 10^6$ CFU/mL to about $1 \times 10^{11}$ CFU/mL. In certain embodiments, the *Methylobacterium* in the liquid or emulsion are at a titer of about $5 \times 10^8$ CFU/mL to about $1 \times 10^{11}$ CFU/mL. In certain embodiments, the adherent *Methylobacterium* are at a titer of at least about $5 \times 10^8$ CFU/gm to at least about $1 \times 10^{14}$ CFU/gm and the composition is depleted of substances that promote growth of resident microorganisms on a plant or seed. In certain embodiments, substance that promotes growth of resident microorganisms on a plant or seed is selected from the group consisting of a carbon source, a nitrogen source, a phosphorous source, a sulfur source, a magnesium source, and combinations thereof. In certain embodiments, the composition comprises an agriculturally acceptable adjuvant and/or excipient. In certain embodiments of any of the aforementioned compositions, the *Methylobacterium* is strain NLS0038, NLS0046, NLS0020, NLS0017, NLS0042, NLS0089, NLS0068, NLS0065, NLS0069, NLS0062, NLS0064, NLS0021, NLS0066, or NLS0037. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0037 (NRRL B-50941), NLS0038 (NRRL B-50942), NLS0042 (NRRL B-50932), NLS0062 (NRRL B-50937), and derivatives thereof. In certain embodiments of any of the aforementioned compositions, the solid substance with adherent *Methylobacterium* grown thereon is not a substance that promotes growth of resident microorganisms on a plant or seed. In certain embodiments of any of the aforementioned compositions, the composition is adapted for use in treating a plant or seed. Also provided herein is a plant part or plant seed that is coated or partially coated with any of the aforementioned compositions. Methods of treating plants and/or plant parts with the compositions are also provided herein. Treated plants, treated plant parts thereof, include, but are not limited to, corn, *Brassica* sp. (e.g., *B. napus, B. rapa, B. juncea*), alfalfa, rice, rye, sorghum, millet (e.g., pearl millet (*Pennisetum glaucum*), proso millet (*Panicum miliaceum*), foxtail millet (*Setaria italica*), finger millet (*Eleusine coracana*)), sunflower, safflower, soybean, tobacco, potato, peanuts, cotton, sweet potato (*Ipomoea batatus*), cassava, coffee, coconut, pineapple, citrus trees, cocoa, tea, banana, avocado, fig, guava, mango, olive, papaya, cashew, macadamia, almond, sugar beets, sugarcane, oats, barley, tomatoes lettuce, green beans, lima beans, peas, cucurbits such as cucumber, cantaloupe, and musk melon, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, hydrangea, hibiscus, roses, tulips, daffodils, petunias, carnation, poinsettia, and chrysanthemum. Conifer plants and plant parts that can be treated include, but are not limited to, pines such as loblolly pine, slash pine, ponderosa pine, lodgepole pine, and Monterey pine; Douglas-fir; Western hemlock; Sitka spruce; redwood; true firs such as silver fir and balsam fir; and cedars such as Western red cedar and Alaska yellow-cedar. Turfgrass plants and plant parts that can be treated include, but are not limited to, annual bluegrass, annual ryegrass, Canada bluegrass, fescue, bentgrass, wheatgrass, Kentucky bluegrass, orchard grass, ryegrass, redtop, Bermuda grass, St. Augustine grass, and zoysia grass. Seeds or other propagules of any of the aforementioned plants can be treated with the compositions provided herein. In certain embodiments, the *Methylobacterium* in the composition or that is used is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments, the *Methylobacterium* in the composition or that is used is selected from the group consisting of NLS0037 (NRRL B-50941), NLS0038 (NRRL B-50942), NLS0042 (NRRL B-50932), NLS0062 (NRRL B-50937), and derivatives thereof.

DESCRIPTION

Definitions

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition for treatment of plants and/or plant parts. In certain compositions, an active agent can comprise a mono-culture or co-culture of *Methylobacterium*.

As used herein, the phrase "agriculturally acceptable excipient" refers to an essentially inert substance that can be used as a diluent and/or carrier for an active agent in a composition for treatment of plants and/or plant parts. In certain compositions, an active agent can comprise a mono-culture or co-culture of *Methylobacterium*.

As used herein, the term "*Methylobacterium*" refers to bacteria that are facultative methylotrophs of the genus *Methylobacterium*. The term *Methylobacterium*, as used herein, thus does not encompass includes species in the genera *Methylobacter, Methylomonas, Methylomicrobium, Methylococcus, Methylosinus, Methylocystis, Methylosphaera, Methylocaldum,* and *Methylocella*, which are obligate methanotrophs.

As used herein, the phrase "co-culture of *Methylobacterium*" refers to a *Methylobacterium* culture comprising at least two strains of *Methylobacterium* or at least two species of *Methylobacterium*.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the phrase "derivatives thereof", when used in the context of a *Methylobacterium* strain, refers to any strain that is obtained from the *Methylobacterium* strain. Derivatives of a *Methylobacterium* strain include, but are not limited to, variants of the strain obtained by selection, variants of the strain selected by mutagenesis and selection, and genetically transformed isolates obtained from the *Methylobacterium* strain.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is liquid that is not miscible, or partially miscible, in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, the term "peptide" refers to any polypeptide of 50 amino acid residues or less.

As used herein, the term "pepper" refers to *Capsicum* sp. plants. *Capsicum* sp. plants include, but are not limited to, *C. annuum, C. baccatum, C. chinense, C. frutescens,* and *C. pubescens*.

As used herein, the term "protein" refers to any polypeptide having 51 or more amino acid residues.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of said *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans.*

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

As used herein, the phrase "substantially all of the solid phase is suspended in the liquid phase" refers to media wherein at least 95%, 98%, or 99% of solid substance(s) comprising the solid phase are distributed throughout the liquid by agitation.

As used herein, the phrase "substantially all of the solid phase is not suspended in the liquid phase" refers to media where less than 5%, 2%, or 1% of the solid is in a particulate form that is distributed throughout the media by agitation.

As used herein, the phrase "resident microorganism" refers to resident bacteria, fungi or yeast.

As used herein, the phrase "substance that promotes growth of resident microorganisms on a plant or seed" refers to a carbon source, a nitrogen source, a phosphorous source, and combinations thereof.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

*Methylobacterium*-Containing Compositions Depleted of Substances that Promote Growth of Resident Bacteria on a Plant or Seed, Methods of their Use, and Methods of Making Compositions comprising *Methylobacterium* that are depleted of substances that promote growth of resident bacteria on a plant or seed, methods of using the compositions to improve fruit production, and methods of making the compositions are provided herein. In certain embodiments of any of the aforementioned compositions, the composition comprises a solid substance wherein a mono-culture or co-culture of *Methylobacterium* is adhered thereto. In certain embodiments where the *Methylobacterium* is adhered to a solid substance, the composition comprises a colloid formed by the solid substance wherein a mono-culture or co-culture of *Methylobacterium* is adhered thereto and a liquid. In certain embodiments, the colloid is a gel. In certain embodiments of certain aforementioned compositions, composition is an emulsion that does not contain a solid substance.

Compositions that comprise a solid substance with adherent *Methylobacterium* grown thereon is provided. In certain embodiments, the adherent *Methylobacterium* can be at a titer of at least about $5\times10^8$ CFU/gm to at least about $5\times10^{13}$ CFU/gm or about $1\times10^{14}$ CFU/gm and the composition is depleted of substances that promote growth of resident microorganisms on a plant or seed.

In certain embodiments, the compositions containing *Methylobacterium* provided or used herein are depleted of substances that promote growth of the resident microorganisms when one or more of those substances are absent or are essentially absent. In certain embodiments, the composition is depleted of substances that promote growth of the resident microorganisms when those substances are present at a percentage of no more than about 5%, 2%, 1%, 0.5%, 0.2%, or 0.1% of the total mass, mass/total volume, or total volume of the composition. In certain embodiments, substance that promotes growth of resident microorganisms on a plant or seed is selected from the group consisting of a carbon source, a nitrogen source, a phosphorous source, a sulfur source, a magnesium source, and combinations thereof. Carbon sources include, but are not limited to, alcohols, monosaccharides, disaccharides, polysaccharides, lipids, fatty acids, and the like. Alcohols that are depleted include, but are not limited to, methanol, ethanol, glycerol, and the like. Nitrogen sources include, but are not limited to, ammonia and various compounds containing amino groups that can be metabolized by microorganisms. In certain embodiments, the substance that is depleted is a source of two or more of a carbon source, a nitrogen source, a phosphorous source, a sulfur source, and a magnesium source. For example, the composition that is depleted of amino acids or peptides and lacks other carbon or nitrogen sources is depleted for both a carbon and a nitrogen source. In certain embodiments, the composition comprises an agriculturally acceptable adjuvant and/or excipient.

Resident microorganisms on the plant or seed include, but are not limited to bacteria, fungi, and yeast. Substances that promote the growth of such microorganisms can be identified by methods including, but not limited to, assaying the plant or seed surface for the amount or number of microorganisms present prior to exposure of the plant or seed to the substance (or to a composition containing the substance), exposing the assayed plant or seed to the substance or composition in parallel with a control composition lacking the substance, and then re-assaying the plant or seed surface for the amount or number of microorganisms present after a suitable time interval and under suitable conditions of temperature to allow growth of the resident microorganisms. Assays for numbers of microorganisms include, but are not limited to, determinations of colony forming units per an amount of plant or seed exposed to the substance and the control.

Without seeking to be limited by theory, it is believed that the compositions containing *Methylobacterium* provided or used herein that are depleted of substances that promote growth of the resident microorganisms can result in superior results in comparison to other compositions containing such substances when applied to plants, plant parts, or seeds. Such superior results are believed to include, but are not limited to, improved plant yield, fruit ripening and the like. While not seeking to be limited by theory, it is believed that the compositions containing *Methylobacterium* that are depleted of substances that promote growth of the resident microorganisms allow for more efficient and or extensive colonization of the plant, part thereof, or seed as competition for one or more of space or nutrients by the resident microorganisms is reduced.

Also provided herein are methods for improving fruit production that comprise applying any of the aforementioned compositions provided herein to a fruit bearing plant, plant part, or seed, and harvesting fruit from the plant or a plant grown from the seed. In certain embodiments, the composition coats or partially coats the fruit bearing plant, plant part, or seed. The plant or plant grown from the seed exhibits faster fruit set, increased fruit set, earlier maturation, and/or produces more mature fruit compared to an untreated control plant, thereby obtaining improved fruit production. In certain embodiments, the fruit that is produced by the methods and compositions provided herein exhibit more uniform fruit maturation in that more fruit ripen within a shorter time span in comparison to fruit produced by an untreated control plant. The increased uniformity of fruit maturation provided herein can permit harvest of fruit that is more uniform in its degree of ripening, such that fewer unripe, under-ripened, and/or over-ripened fruit are harvested in comparison to fruit harvested from an untreated control plant. In certain embodiments, application of the compositions provides for about a 5% or 10% to about a 15%, 20%, 25%, 30%, 35%, 50%, 60%, 75% or 80% increase in the number of ripened fruit present during a given time span in the treated plant, plant part, or a plant derived therefrom in comparison to the untreated control plant, plant part, or plant obtained therefrom. In certain embodiments, application of the compositions provides for about a 5% or 10% to about a 15%, 20%, 25%, 30%, 35%, 50%, 60%, 75% or 80% decrease in the number of unripe, under-ripened, and/or over-ripened fruit harvested from the treated plant, plant part, or a plant derived therefrom in comparison to the untreated control plant, plant part, or plant obtained therefrom. In certain embodiments, application of the composition provides for at least about a 5%, 10%, 15% or 20% decrease in the time to fruit set or to fruit maturation in the plant, plant part, or a plant derived therefrom in comparison to the untreated control plant, plant part, or plant obtained therefrom. In certain embodiments, application of the composition provides for about a 5% or 10% to about a 15%, 20%, 25%, 30%, or 35% increase in fruit set or in production of mature fruit in the plant, plant part, or a plant derived therefrom in comparison to the untreated control plant, plant part, or plant obtained therefrom. In certain embodiments, application of the composition provides for at least about a 5%, 10%, 15% or 20% decrease in the time to fruit set or fruit maturation in the plant, plant part, or a plant derived therefrom in comparison to the untreated control plant, plant part, or plant obtained therefrom. In certain embodiments, application of the composition provides for about a 5% or 10% to about a 15%, 20%, 25%, 30%, or 35% increase in fruit set or production of mature fruit in the plant, plant part, or a plant derived therefrom in comparison to the untreated control plant, plant part, or plant obtained therefrom. In certain embodiments, the fruit bearing plant is an apple, pear, grape, citrus, melon, pepper, tomato, berry, kiwi, mango, or banana plant, and the plant part is a leaf, a stem, a flower, a root, a tuber, or a seed. In certain embodiments, the berry plant is a blackberry, strawberry, or blueberry plant. In certain embodiments, the plant is a pepper plant. In certain embodiments, the method further comprises the steps of growing the plant and/or the step of harvesting at least one plant part selected from the group consisting of a leaf, a stem, a flower, a root, a tuber, or a seed from the plant or plant part. In certain embodiments of any of the aforementioned methods, the methods further comprise obtaining a processed food or feed composition from the plant or plant part. In certain embodiments, the processed food or feed composition is a meal or a paste.

Also provided are methods of making a plant or plant seed treatment composition that comprises *Methylobacterium* and is depleted of substances that promote growth of resident bacteria on a plant or seed is provided herein. Such method comprises (i) growing a mono-culture or co-culture of *Methylobacterium* in media that comprises an aqueous phase, a liquid phase and a solid phase, or an emulsion, thereby obtaining a *Methylobacterium*-containing media; (ii) separating the *Methylobacterium* from at least one other portion of the *Methylobacterium*-containing media; and (iii) reconstituting the *Methylobacterium* in a matrix lacking substances that promote growth of resident bacteria on a plant or seed. In certain embodiments, the separation step is effected by centrifugation, filtration, or settling of the *Methylobacterium*-containing media and removal of excess liquid or emulsion therefrom. In certain embodiments, the substance that promotes growth of resident bacteria on a plant or seed is selected from the group consisting of a carbon source, a nitrogen source, a phosphorous source, and combinations thereof. In certain embodiments, the matrix is a liquid, an emulsion, or one or more solids, and comprises an agriculturally acceptable adjuvant and/or excipient. Still in certain embodiments; the *Methylobacterium* are grown in media comprising a liquid phase and a solid substance with adherent *Methylobacterium* grown thereon. The solid substance is separated from the liquid phase of the *Methylobacterium*-containing media, and the solid substance with adherent *Methylobacterium* grown thereon is reconstituted in the aforementioned matrix. In certain embodiments of the methods, the *Methylobacterium* sp., is selected from the group consisting of *M. aminovorans, M. extorquens, M. fujisawaense, M. mesophilicum, M. radiotolerans, M. rhodesianum, M. nodulans, M. phyllosphaerae, M. thiocyanatum*, and *M. oryzae*. In certain embodiments of the methods, the *Methylobacterium* is not *M. radiotolerans* or *M. oryzae*. In certain embodiments of the methods, the *Methylobacterium* is adhered to a solid substance. In certain embodiments of the methods, the *Methylobacterium* is adhered to the solid substance is combined with a liquid to form a composition that is a colloid. In certain embodiments of the methods, the colloid is a gel. In certain embodiments of the methods, the *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion.

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the media comprises a colloid formed by a solid and a liquid phase. A colloid comprising a solid and a liquid can be pre-formed and added to liquid media or can be formed in media containing a solid and a liquid. Colloids comprising a solid and a liquid can be formed by subjecting certain solid substances to a chemical and/or thermal change. In certain embodiments, the colloid is a gel. In certain embodiments, the liquid phase of the media is an emulsion. In certain embodiments, the emulsion comprises an aqueous liquid and a liquid that is not miscible, or only partially miscible, in the aqueous liquid. Liquids that are not miscible, or only partially miscible, in water include, but are not limited to, any of the following: (1) liquids having a miscibility in water that is equal to or less than that of pentanol, hexanol, or heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5 carbons and sterols; (4) an animal oil, microbial oil, synthetic oil, plant oil, or combination thereof; and/or, (5) a plant oil is selected from the group consisting of corn, soybean, cotton, peanut, sunflower, olive, flax, coconut, palm, rapeseed, sesame seed, safflower, and combinations thereof. In certain embodiments, the immiscible or partially immiscible liquid can comprises at least about 0.02% to about 20% of the liquid phase by mass. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). Methods and compositions for growing *Methylobacterium* in biphasic media comprising a liquid and a solid are disclosed in co-assigned U.S. patent application Ser. No. 13/907,161, filed May 31, 2013, which is incorporated herein by reference in its entirety, and in co-assigned International Patent Application PCT/US13/43722, filed May 31, 2013, which is incorporated herein by reference in its entirety.

Methods where *Methylobacterium* are cultured in media comprising an emulsion have also been found to significantly increase the resultant yield of *Methylobacterium* relative to methods where the *Methylobacterium* are cultured in liquid media alone. In certain embodiments, the methods for making the compositions provided herein can comprise growing the *Methylobacterium* agent in an emulsion under conditions that provide for *Methylobacterium* growth. Medias comprising the emulsion and *Methylobacterium* can be obtained by a variety of methods that include, but are not limited to, any of: (a) inoculating a media comprising the emulsion with *Methylobacterium*; (b) inoculating the aqueous liquid with the *Methylobacterium*, introducing the non-aqueous liquid, and mixing to form an emulsion; (c) inoculating the aqueous liquid with the *Methylobacterium*, introducing the non-aqueous liquid, and mixing to form an emulsion; or (d) any combination of (a), (b), or (c). In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof; (3) alcohols is selected from the group consisting of aliphatic alcohols containing at least 5, 6, or 7 carbons and sterols; (4) an animal oil, microbial oil, synthetic oil, plant oil, or combination thereof; and/or, (5) a plant oil is selected from the group consisting of corn, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass. Methods and compositions for growing *Methylobacterium* in media comprising an emulsion are disclosed in co-assigned International Patent Application PCT/US2014/040218, filed May 30, 2014, which is incorporated herein by reference in its entirety.

In certain embodiments, the fermentation broth, fermentation broth product, or compositions that comprise *Methylobacterium* sp. can further comprise one or more introduced microorganisms of pre-determined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma virens*, and *Streptomyces lydicus* strains. Other microorganisms that are added can be genetically engineered or wild typeisolates that are available as pure cultures. In certain embodiments, it is anticipated that the bacterial or fungal microorganism can be provided in the fermentation broth, fermentation broth product, or composition in the form of a spore.

In certain embodiments, the liquid culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Exemplary liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria-Bertani Broth").

The solid substance used in the methods and compositions that provide for the efficient growth of *Methylobacterium* can be any suitable solid substance which is insoluble or only partially soluble in water or aqueous solutions. Such suitable solid substances are also non-bacteriocidal or non-bacteriostatic with respect to *Methylobacterium* when the solid substances are provided in the liquid culture media. In certain embodiments, such suitable solid substances are also solid substances that are readily obtained in sterile form or rendered sterile. Solid substances used herein can be sterilized by any method that provides for removal of contaminating microorganisms and thus include, but are not limited to, methods such as autoclaving, irradiation, chemical treatment, and any combination thereof. These solid substances include natural substances of animal, plant, microbial, fungal, or mineral origin, manmade substances, or combinations of natural and manmade substances. In certain embodiments, the solid substances are inanimate solid substances. Inanimate solid substances of animal, plant, microbial, or fungal origin can be obtained from animals, plants, microbes, or fungi that are unviable (i.e. no longer living) or that have been rendered unviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (e.g. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In certain embodiments, the microbial cell or microbial spore is not a photosynthetic microorganism, where the photosynthetic microorganism is selected from the group consisting of algae, cyanobacteria, diatoms, *Botryococcus braunii*, *Chlorella*, *Dunaliella tertiolecta*, *Gracilaria*, *Pleurochrysis camerae*, *Sargassum*, and *Ulva*. In still other embodiments, the solid substance can be an inactivated (i.e., unviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, barks, seeds, and combinations thereof. Products obtained from processed plant parts including, but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, the solid substance is provided in the media as a colloid wherein the continuous phase is a liquid and the dispersed phase is the solid. Suitable solids that can be used to form colloids in liquid media used to grow *Methylobacterium* include, but are not limited to, various solids that are referred to as hydrocolloids. Such hydrocolloids used in the media, methods and compositions provided herein can be hydrophilic polymers, of plant, animal, microbial, or synthetic origin. Hydrocolloid polymers used in the methods can contain many hydroxyl groups and/or can be polyelectrolytes. Hydrocolloid polymers used in the compositions and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. In certain embodiments, the colloid used in the media, methods, and compositions provided herein can comprise a hydrocolloid polymer and one or more proteins.

In certain embodiments, the solid substance can be a solid substance that provides for adherent growth of *Methylobacterium* on the solid substance. *Methylobacterium* that are adhered to a solid substance are *Methylobacterium* that cannot be substantially removed by simply washing the solid substance with the adherent *Methylobacterium* with growth media whereas non-adherent *Methylobacterium* can be substantially removed by washing the solid substance with liquid growth media. In this context, "substantially removed" means that at least about 30%, 40%, 50%, 60%, 70%, or 80% the *Methylobacterium* present are removed when the solid substance is washed with three volumes of liquid growth media. Such washing can be effected by a variety of methods including, but not limited to, decanting liquid from a washed solid phase or passing liquid through a solid phase on a filter that permits flow through of bacteria in the liquid. In certain embodiments, the adherent *Methylobacterium* that are associated with the solid can include both *Methylobacterium* that are directly attached to the solid and/or *Methylobacterium* that are indirectly attached to the solid substance. *Methylobacterium* that are indirectly attached to the solid substance include, but are not limited to, *Methylobacterium* that are attached to another *Methylobacterium* or to another microorganism that is attached to the solid substance, *Methylobacterium* that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent *Methylobacterium* can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 1 *Methylobacterium*/10 square micrometers, of at least about 1 *Methylobacterium*/5 square micrometers, of at least about 1 *Methylobacterium*/2 square micrometers, or of at least about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Biphasic fermentation broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml.

Biphasic culture methods provided can yield fermentation broths with *Methylobacterium* at a titer of greater than about $5 \times 10^8$ colony-forming units per milliliter, at a titer of greater than about $1 \times 10^9$ colony-forming units per milliliter, at a titer of greater than about $1 \times 10^{10}$ colony-forming units per milliliter, at a titer of at least about $3 \times 10^{10}$ colony-forming units per milliliter. In certain embodiments, fermentation broths provided herein can comprise *Methylobacterium* at a titer of at least about $5 \times 10^8$ colony-forming units per milliliter to at least about $3 \times 10^{10}$ colony-forming units per milliliter, at least about $5 \times 10^8$ colony-forming units per milliliter to at least about $4 \times 10^{10}$ colony-forming units per milliliter, or at least about $5 \times 10^8$ colony-forming units per milliliter to at least about $6 \times 10^{10}$ colony-forming units per milliliter. In certain embodiments, fermentation broths provided herein can comprise *Methylobacterium* at a titer of at least about $1 \times 10^9$ colony-forming units per milliliter to at least about $3 \times 10^{10}$ colony-forming units per milliliter, at least about $1 \times 10^9$ colony-forming units per milliliter to at least about $4 \times 10^{10}$ colony-forming units per milliliter, or at least about $1 \times 10^9$ colony-forming units per milliliter to at least about $6 \times 10^{10}$ colony-forming units per milliliter. In certain embodiments, fermentation broths provided herein will comprise *Methylobacterium* at a titer of at least about $1 \times 10^{10}$ colony-forming units per milliliter to at least about $3 \times 10^{10}$ colony-forming units per milliliter, at least about $1 \times 10^{10}$ colony-forming units per milliliter to at least about $4 \times 10^{10}$ colony-forming units per milliliter, or at least about $1 \times 10^{10}$ colony-forming units per milliliter to at least about $6 \times 10^{10}$ colony-forming units per milliliter. In certain embodiments, fermentation broths provided herein will comprise *Methylobacterium* at a titer of, at least about $3 \times 10^{10}$ colony-forming units per milliliter to at least about $4 \times 10^{10}$ colony-forming units per milliliter, or at least about $3 \times 10^{10}$ colony-forming units per milliliter to at least about $6 \times 10^{10}$ colony-forming units per milliliter.

Solid substances with adherent *Methylobacterium* can be obtained as fermentation products can be used to make various compositions useful for treating plants or plant parts to improve plant yield, and/or improve fruit production of fruit bearing plant. In certain embodiments, the composition comprises *Methylobacterium* and is depleted of substances that promote growth of resident bacteria. Compositions provided herein comprising *Methylobacterium*, solid substances with *Methylobacterium* grown thereon, or comprising emulsions with *Methylobacterium* grown therein can be used to treat plants or plant parts. Plants, plant parts, and, in particular, plant seeds that have been at least partially coated or coated with the fermentation broth products or compositions comprising *Methylobacterium* are thus provided. Also provided are processed plant products that contain the fermentation broth products or compositions with *Methylobacterium* or adherent *Methylobacterium*. Solid substances with adherent *Methylobacterium* can be used to make various compositions that are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the solid substance used in the fermentation product or composition that at least partially coats the plant, plant part, or plant seed or that is contained in the processed plant, plant part, or seed product comprises a solid substance and associated or adherent *Methylobacterium* that can be readily identified by comparing a treated and an untreated plant, plant part, plant seed, or processed product thereof. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed.

Methods of preparing a plant or plant seed treatment composition that comprises *Methylobacterium* and is depleted of substances that promote growth of resident bacteria on a plant or seed are also provided herein. Such methods can comprise (i) growing a mono-culture or co-culture of *Methylobacterium* in media that comprises: (a) an aqueous phase; (b) a liquid phase and a solid phase; or (c) an emulsion, thereby obtaining a *Methylobacterium*-containing media; (ii) separating the *Methylobacterium* from at least one other portion of the *Methylobacterium*-containing media; and (iii) reconstituting the *Methylobacterium* in a matrix lacking substances that promote growth of resident bacteria on a plant or seed. In certain embodiments, the separation step is effected by centrifugation, filtration, or settling of the *Methylobacterium*-containing media and removal of excess liquid or emulsion therefrom. In certain embodiments where the *Methylobacterium* are grown in the presence of a solid substance, the separation will provide a fraction containing *Methylobacterium* with adherent growth to the solid substance and some non-adherent *Methylobacterium* that can be reconstituted in the matrix. In certain embodiments, the substance that promotes growth of resident bacteria on a plant or seed is selected from the group consisting of a carbon source, a nitrogen source, a phosphorous source, a sulfur source, a magnesium source, and combinations thereof. In certain embodiments, the matrix is a liquid, an emulsion, or one or more solids, and comprises an agriculturally acceptable adjuvant and/or excipient. In certain embodiments; the *Methylobacterium* are grown in media comprising a liquid phase and a solid substance with adherent *Methylobacterium* grown thereon. The solid substance is separated from the liquid phase of the *Methylobacterium*-containing media, and the solid substance with adherent *Methylobacterium* grown thereon is reconstituted in the aforementioned matrix. In certain embodiments, the matrix can be a liquid including, but not limited to, water, and aqueous buffer depleted of substances that promote growth of resident bacteria on a plant or seed, or an aqueous solution depleted of substances that promote growth of resident bacteria on a plant or seed.

Also provided herein are compositions comprising any of the following *Methylobacterium* sp. isolates provided in the following Table 1, as well as plants, plant parts, and plant seeds that are coated or partially coated with the compositions.

TABLE 1

*Methylobacterium* sp. isolates

| ISOLATE No. | NLS No. | USDA ARS NRRL No.[1] |
|---|---|---|
| ISO01 | NLS0046 | NRRL B-50929 |
| ISO02 | NLS0020 | NRRL B-50930 |
| ISO03 | NLS0017 | NRRL B-50931 |
| ISO04 | NLS0042 | NRRL B-50932 |
| ISO05 | NLS0089 | NRRL B-50933 |
| ISO06 | NLS0068 | NRRL B-50934 |
| ISO07 | NLS0065 | NRRL B-50935 |
| ISO08 | NLS0069 | NRRL B-50936 |
| ISO09 | NLS0062 | NRRL B-50937 |
| ISO10 | NLS0064 | NRRL B-50938 |
| ISO11 | NLS0021 | NRRL B-50939 |
| ISO12 | NLS0066 | NRRL B-50940 |

TABLE 1-continued

*Methylobacterium* sp. isolates

| ISOLATE No. | NLS No. | USDA ARS NRRL No.[1] |
|---|---|---|
| ISO13 | NLS0037 | NRRL B-50941 |
| ISO14 | NLS0038 | NRRL B-50942 |

[1]Deposit number for strain deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Co-assigned patent applications that disclose additional specific uses of the *Methylobacterium* strains of Table 1 such as: (1) increasing corn yield (U.S. 61/911,780, filed Dec. 4, 2013; and International Application claiming benefit of the same filed on Dec. 4, 2014); (2) increasing soybean yield (U.S. 61/911,698, filed Dec. 4, 2013; and International Application claiming benefit of the same filed on Dec. 4, 2014); (3) improving lettuce cultivation (International Patent Application PCT/US14/68558, filed on Dec. 4, 2014); (4) improving tomato growth (International Patent Application PCT/US14/68611 filed on Dec. 4, 2014) and are each incorporated herein by reference in their entireties. Specifically incorporated herein by reference in their entireties are the amino acid and genomic nucleic acid sequences of *Methylobacterium* sp. NLS017, NLS020, NLS037, NLS042, NLS065, and NLS066 that are disclosed in International Patent Application PCT/US14/68558, filed on Dec. 4, 2014. Also specifically incorporated herein by reference in their entireties are the amino acid and genomic nucleic acid sequences of *Methylobacterium* sp. NLS017 and NLS066 disclosed in the International Patent Application PCT/US14/68611 filed on Dec. 4, 2014. Such amino acid and genomic nucleic acid sequences can be used to identify compositions, plant parts, plant seeds, or processed plant products comprising *Methylobacterium* sp. NLS017, NLS020, NLS037, NLS042, NLS065, and NLS066.

Compositions provided herein that are useful for treating plants or plant parts that comprise *Methylobacterium*, and/or are depleted of substances that promote growth of resident bacteria on a plant or seed, contain a solid substance with adherent *Methylobacterium* grown thereon, or that comprise emulsions with *Methylobacterium* grown therein can also further comprise an agriculturally acceptable adjuvant or an agriculturally acceptable excipient. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, an insecticide, a fungicide, a nematocide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension. Any of the compositions provided herein can be used to coat or partially coat a plant, plant, part, or plant seed. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed.

Agriculturally acceptable adjuvants used in the compositions that comprise *Methylobacterium* include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants that can promote contact of the active agent with interior tissues, extenders that increase the half-life of the active agent by inhibiting environmental degradation, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/defoaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions comprising *Methylobacterium* are also provided herein. Treated plants, and treated plant parts obtained therefrom, include, but are not limited to, a pepper, tomato, berry, or banana plant. Plant parts that are treated include, but are not limited to, leaves, stems, flowers, roots, seeds, fruit, tubers, coleoptiles, and the like. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions that comprise *Methylobacterium* as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (e.g. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a biphasic fermentation broth, a fermentation broth product, fermentation product, or compositions that comprise a solid substance with *Methylobacterium* adhered thereto are also provided herein. Also provided herein are processed plant products that comprise a solid substance with *Methylobacterium* adhered thereto. Any of the compositions provided herein can be used to coat or partially coat a plant, plant, part, or plant seed. Partial coating of a plant, a plant part, or a seed includes, but is not limited to coating at least about 5%, 10%, 20%, 30%, 40%, 50%, 60%, 70%, 80%, 90%, 95%, 98%, 99%, or about 99.5% of the surface area of the plant, plant part, or plant seed In certain embodiments, seeds are treated by exposing the seeds to the fermentation broths, fermentation broth products, fermentation products, and compositions that comprise *Methylobacterium* Seeds can be treated with the fermentation broths, fermentation broth products, and compositions provided herein by methods including, but not limited to, imbibition, coating, spraying, and the like. In certain embodiments, surface sterilized seeds are treated with a composition comprising *Methylobacterium*. In certain embodiments, non-sterilized seeds (e.g. seeds that have not been subjected to surface sterilization) are treated with a composition comprising *Methylobacterium* that has been depleted of substances that promote growth of resident microorganisms on the seed. Seed treatments can be effected with both continuous and/or a batch seed treaters. In certain embodiments, the coated seeds can be prepared by slurrying seeds with a coating composition containing a fermentation broth, fermentation broth product, or compositions that comprise the solid substance with *Methylobacterium* and air drying the resulting product. Air drying can be accomplished at any temperature that is not deleterious to the seed or the *Methylobacterium*, but will typically not be greater than 30 degrees Centigrade. The proportion of coating that comprises a solid substance and *Methylobacterium* includes, but is not limited to, a range of 0.1 to 25% by weight of the seed, 0.5 to 5% by weight of the seed, and 0.5 to 2.5% by weight of seed. Partial coating of a seed can includes, but is not limited to coating at least about 5%, 10%, 20%, 30%, 40%, 50%, 60%, 70%, 80%, 90%, 95%, 98%, 99%, or about 99.5% of the surface area of the seed. In certain embodiments, a solid substance used in the seed coating or treatment will have *Methylobacterium* adhered thereon. In certain embodiments, a solid substance used in the seed coating or treatment will be associated with *Methylobacterium* and will be a fermentation broth, fermentation broth product, or composition obtained by the methods provided herein. Various seed treatment compositions and methods for seed treatment disclosed in U.S. Pat. Nos. 5,106,648, 5,512,069, and 8,181,388 are incorporated herein by reference in their entireties and can be adapted for use with an active agent comprising the fermentation broths, fermentation broth products, or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with an active agent comprising the fermentation broths, fermentation broth products, or compositions provided herein.

Provided herein are compositions that comprise *Methylobacterium* that provide improved plant yield, as well as improved fruit production of fruit bearing plants relative to untreated plants that have not been exposed to the compositions. In certain embodiments, plant parts, including, but not limited to, a seed, a leaf, a fruit, a stem, a root, a tuber, or a coleoptile can be treated with the compositions provided herein to improve plant yield, insect control, fungal control, and/or fruit production. Treatments or applications can include, but are not limited to, spraying, coating, partially coating, immersing, and/or imbibing the plant or plant parts with the compositions provided herein. In certain embodiments, a seed, a leaf, a fruit, a stem, a root, a tuber, or a coleoptile can be immersed and/or imbibed with a liquid, semi-liquid, emulsion, or slurry of a composition provided herein. Such seed immersion or imbibition can be sufficient to provide for improved plant yield, insect control, fungal control, and/or fruit production in a treated plant or plant part in comparison to an untreated plant or plant part. Improved fruit production includes, but is not limited to faster fruit set, increased fruit set, earlier maturation, and/or production of more mature fruit relative to untreated plants. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Compositions provided herein comprising *Methylobacterium* are therefore expected to be useful in improving fruit production in a wide variety of plants, including, but not limited to: an apple, pear, grape, citrus, melon, pepper, tomato, berry, kiwi, mango, or banana plant. In certain embodiments, the berry plant is a blackberry, strawberry, or blueberry plant. Compositions provided herein comprising *Methylobacterium* are therefore expected to be useful in improving plant yield, insect control in plants, and control of plant pathogenic fungi in a wide variety of plants, including, but not limited to: corn, *Brassica* sp. (e.g., *B. napus, B. rapa, B. juncea*), alfalfa, rice, rye, sorghum, millet (e.g., pearl millet (*Pennisetum glaucum*), proso millet (*Panicum miliaceum*), foxtail millet (*Setaria italica*), finger millet (*Eleusine coracana*)), sunflower, safflower, soybean, tobacco, potato, peanuts, cotton, sweet potato (*Ipomoea batatus*), cassava, coffee, coconut, pineapple, citrus trees, cocoa, tea, banana, avocado, fig, guava, mango, olive, papaya, cashew, macadamia, almond, sugar beets, sugarcane, oats, barley, tomatoes lettuce, green beans, lima beans, peas, cucurbits such as cucumber, cantaloupe, and musk melon, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, hydrangea, hibiscus, roses, tulips, daffodils, petunias, carnation, poinsettia, and chrysanthemum. Conifer plants and plant parts that can be treated include, but are not limited to, pines such as loblolly pine, slash pine, ponderosa pine, lodgepole pine, and Monterey pine; Douglas-fir; Western hemlock; Sitka spruce; redwood; true firs such as silver fir and balsam fir; and cedars such as Western red cedar and Alaska yellow-cedar. Turfgrass plants and plant parts that can be treated include, but are not limited to, annual bluegrass, annual ryegrass, Canada bluegrass, fescue, bentgrass, wheatgrass, Kentucky bluegrass, orchard grass, ryegrass, redtop, Bermuda grass, St. Augustine grass, and zoysia grass. Seeds or other propagules of any of the aforementioned plants can be treated with the compositions provided herein.

In certain embodiments, an amount of a composition provided herein that is sufficient to provide for improved plant yield, improved insect control in plants, improved control of plant pathogenic fungi in plants, as well as improved fruit production can be a composition with *Methylobacterium* at a titer of at least about $1 \times 10^6$ colony-forming units per milliliter, at least about $5 \times 10^6$ colony-forming units per milliliter, at least about $1 \times 10^7$ colony-forming units per milliliter, at least about $5 \times 10^8$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, an amount of a composition provided herein that is sufficient to provide for improving plant yield and/or fruit production can be a composition with *Methylobacterium* at a titer of about least about $1 \times 10^6$ colony-forming units per milliliter, at least about $5 \times 10^6$ colony-forming units per milliliter, at least about $1 \times 10^7$ colony-forming units per milliliter, or at least about $5 \times 10^8$ colony-forming units per milliliter to at least about $6 \times 10^{10}$ colony-forming units per milliliter of a liquid or an emulsion. In certain embodiments, an amount of a composition provided herein that is sufficient to provide for improving plant yield, and/or fruit production can be a fermentation broth product with a *Methylobacterium* titer of a solid phase of that product is at least about $5\times10^8$ colony-forming units per milliliter to at least about $5\times10^{13}$ colony-forming units of *Methylobacterium* per gram of the solid phase. In certain embodiments, an amount of a composition provided herein that is sufficient to provide for improving plant yield, and/or fruit production can be a composition with a *Methylobacterium* titer of at least about $1\times10^6$ colony-forming units per gram, at least about $5\times10^6$ colony-forming units per gram, at least about $1\times10^7$ colony-forming units per gram, or at least about $5\times10^8$ colony-forming units per gram to at least about $6\times10^{10}$ colony-forming units of *Methylobacterium* per gram of particles in the composition containing the particles that comprise a solid substance wherein a mono-culture or co-culture of *Methylobacterium* is adhered thereto. In certain embodiments, an amount of a composition provided herein that is sufficient to provide for improving plant yield and/or fruit production can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL in a composition comprising an emulsion wherein a mono-culture or co-culture of a *Methylobacterium* adhered to a solid substance is provided therein or grown therein. In certain embodiments, an amount of a composition provided herein that is sufficient to provide for improving plant yield and/or fruit production can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL of in a composition comprising an emulsion wherein a mono-culture or co-culture of a *Methylobacterium* is provided therein or grown therein.

In certain embodiments, an amount of a composition provided herein that is sufficient to provide for improved plant yield and/or fruit production can be a composition with a *Methylobacterium* sp. at a titer of at least about $1\times10^4$ colony-forming units per milliliter, at least about $1\times10^5$ colony-forming units per milliliter, at least about $1\times10^6$ colony-forming units per milliliter, at least about $5\times10^6$ colony-forming units per milliliter, at least about $1\times10^7$ colony-forming units per milliliter, at least about $5\times10^8$ colony-forming units per milliliter, at least about $1\times10^9$ colony-forming units per milliliter, at least about $1\times10^{10}$ colony-forming units per milliliter, or at least about $3\times10^{10}$ colony-forming units per milliliter. In certain embodiments, an amount of a composition provided herein that is sufficient to provide for improved plant yield and/or fruit production can be a composition with *Methylobacterium* sp. at a titer of at least about $1\times10^4$ colony-forming units per milliliter, at least about $1\times10^5$ colony-forming units per milliliter, about least about $1\times10^6$ colony-forming units per milliliter, at least about $5\times10^6$ colony-forming units per milliliter, at least about $1\times10^7$ colony-forming units per milliliter, or at least about $5\times10^8$ colony-forming units per milliliter to at least about $6\times10^{10}$ colony-forming units per milliliter of a liquid or an emulsion. In certain embodiments, an amount of a composition provided herein that is sufficient to provide for improved plant yield and/or fruit production can be a fermentation broth product with a *Methylobacterium* sp. titer of a solid phase of that product is at least about $1\times10^4$ colony-forming units per gram, at least about $1\times10^5$ colony-forming units per gram, at least about $1\times10^6$ colony-forming units per gram, at least about $5\times10^6$ colony-forming units per gram, at least about $1\times10^7$ colony-forming units per gram, at least about $5\times10^8$ colony-forming units per gram, at least about $1\times10^9$ colony-forming units per gram, or at least about $5\times10^9$ colony-forming units per gram to at least about $6\times10^{10}$ colony-forming units of *Methylobacterium* per gram, at least about $1\times10^{11}$ colony-forming units of *Methylobacterium* per gram, at least about $1\times10^{12}$ colony-forming units of *Methylobacterium* per gram, at least about $1\times10^{13}$ colony-forming units of *Methylobacterium* per gram, or at least about $5\times10^{13}$ colony-forming units of *Methylobacterium* per gram of the solid phase. In certain embodiments, an amount of a composition provided herein that is sufficient to provide for improved plant yield and/or fruit production can be a composition with a *Methylobacterium* titer of at least about $1\times10^6$ colony-forming units per gram, at least about $5\times10^6$ colony-forming units per gram, at least about $1\times10^7$ colony-forming units per gram, at least about $5\times10^8$ colony-forming units per gram, at least about $1\times10^9$ colony-forming units per gram, or at least about $5\times10^9$ colony-forming units per gram to at least about $6\times10^{10}$ colony-forming units of *Methylobacterium* per gram, at least about $1\times10^{11}$ colony-forming units of *Methylobacterium* per gram, at least about $1\times10^{12}$ colony-forming units of *Methylobacterium* per gram, at least about $1\times10^{13}$ colony-forming units of *Methylobacterium* per gram, or at least about $5\times10^{13}$ colony-forming units of *Methylobacterium* per gram of particles in the composition containing the particles that comprise a solid substance wherein a mono-culture or co-culture of *Methylobacterium* sp. is adhered thereto. In certain embodiments, an amount of a composition provided herein that is sufficient to provide for improved plant yield and/or fruit production can be a composition with a *Methylobacterium* titer of at least about $1\times10^6$ colony-forming units per mL, at least about $5\times10^6$ colony-forming units per mL, at least about $1\times10^7$ colony-forming units per mL, at least about $5\times10^8$ colony-forming units per mL, at least about $1\times10^9$ colony-forming units per gram, or at least about $5\times10^9$ colony-forming units per gram to at least about $6\times10^{10}$ colony-forming units of *Methylobacterium* per mL in a composition comprising an emulsion wherein a mono-culture or co-culture of a *Methylobacterium* sp. adhered to a solid substance is provided therein or grown therein. In certain embodiments, an amount of a composition provided herein that is sufficient to provide for improved plant yield and/or fruit production can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL of in a composition comprising an emulsion wherein a mono-culture or co-culture of a *Methylobacterium* sp. is provided therein or grown therein.

In certain embodiments, compositions with a *Methylobacterium* sp. at a titer of at least about $1\times10^4$ colony-forming units per milliliter, at least about $1\times10^5$ colony-forming units per milliliter, at least about $1\times10^6$ colony-forming units per milliliter, at least about $5\times10^6$ colony-forming units per milliliter, at least about $1\times10^7$ colony-forming units per milliliter, at least about $5\times10^8$ colony-forming units per milliliter, at least about $1\times10^9$ colony-forming units per milliliter, at least about $1\times10^{10}$ colony-forming units per milliliter, or at least about $3\times10^{10}$ colony-forming units per milliliter are provided or used. In certain embodiments, compositions with *Methylobacterium* sp. at a titer of at least about 1×10⁴ colony-forming units per milliliter, at least about 1×10⁵ colony-forming units per milliliter, about least about 1×10⁶ colony-forming units per milliliter, at least about 5×10⁶ colony-forming units per milliliter, at least about 1×10⁷ colony-forming units per milliliter, or at least about 5×10⁸ colony-forming units per milliliter to at least about 6×10¹⁰ colony-forming units per milliliter of a liquid or an emulsion are provided. In certain embodiments, fermentation broth products with a *Methylobacterium* sp. titer of a solid phase of that product is at least about 1×10⁴ colony-forming units per gram, at least about 1×10⁵ colony-forming units per gram, at least about 1×10⁶ colony-forming units per gram, at least about 5×10⁶ colony-forming units per gram, at least about 1×10⁷ colony-forming units per gram, at least about 5×10⁸ colony-forming units per gram, at least about 1×10⁹ colony-forming units per gram, or at least about 5×10⁹ colony-forming units per gram to at least about 6×10¹⁰ colony-forming units of *Methylobacterium* per gram, at least about 1×10¹¹ colony-forming units of *Methylobacterium* per gram, at least about 1×10¹² colony-forming units of *Methylobacterium* per gram, at least about 1×10¹³ colony-forming units of *Methylobacterium* per gram, or at least about 5×10¹³ colony-forming units of *Methylobacterium* per gram of the solid phase are provided. In certain embodiments, compositions with a *Methylobacterium* titer of at least about 1×10⁶ colony-forming units per gram, at least about 5×10⁶ colony-forming units per gram, at least about 1×10⁷ colony-forming units per gram, at least about 5×10⁸ colony-forming units per gram, at least about 1×10⁹ colony-forming units per gram, or at least about 5×10⁹ colony-forming units per gram to at least about 6×10¹⁰ colony-forming units of *Methylobacterium* per gram, at least about 1×10¹¹ colony-forming units of *Methylobacterium* per gram, at least about 1×10¹² colony-forming units of *Methylobacterium* per gram, at least about 1×10¹³ colony-forming units of *Methylobacterium* per gram, or at least about 5×10¹³ colony-forming units of *Methylobacterium* per gram of particles in the composition containing the particles that comprise a solid substance wherein a mono-culture or co-culture of *Methylobacterium* sp. is adhered thereto are provided. In certain embodiments, compositions with a *Methylobacterium* titer of at least about 1×10⁶ colony-forming units per mL, at least about 5×10⁶ colony-forming units per mL, at least about 1×10⁷ colony-forming units per mL, or at least about 5×10⁸ colony-forming units per mL to at least about 6×10¹⁰ colony-forming units of *Methylobacterium* per mL in a composition comprising an emulsion wherein a mono-culture or co-culture of a *Methylobacterium* sp. adhered to a solid substance is provided therein or grown therein are provided. In certain embodiments, compositions with a *Methylobacterium* titer of at least about 1×10⁶ colony-forming units per mL, at least about 5×10⁶ colony-forming units per mL, at least about 1×10⁷ colony-forming units per mL, or at least about 5×10⁸ colony-forming units per mL to at least about 6×10¹⁰ colony-forming units of *Methylobacterium* per mL of in a composition comprising an emulsion wherein a mono-culture or co-culture of a *Methylobacterium* sp. is provided therein or grown therein is provided. In certain embodiments of any of the aforementioned compositions, the *Methylobacterium* sp. is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), and derivatives thereof. In certain embodiments of any of the aforementioned compositions, the composition can further comprise an agriculturally acceptable adjuvant, an agriculturally acceptable excipient, or combination thereof. In certain embodiments of any of the aforementioned compositions, the *Methylobacterium* sp. is selected from the group consisting of NLS0017 (NRRL B-50931), NLS0020 (NRRL B-50930), NLS0021 (NRRL B-50939), NLS0037 (NRRL B-50941), NLS0038 (NRRL B-50942), NLS0042 (NRRL B-50932), NLS0046 (NRRL B-50929), NLS0062 (NRRL B-50937), NLS0064 (NRRL B-50938), NLS0065 (NRRL B-50935), NLS0066 (NRRL B-50940), NLS0068 (NRRL B-50934), NLS0069 (NRRL B-50936), NLS0089 (NRRL B-50933), derivatives thereof; and also comprises an agriculturally acceptable adjuvant, excipient, or combination thereof. In certain embodiments of any of the aforementioned compositions, the composition is depleted of substances that promote growth of resident microorganisms on a plant or seed. Also provided are plants, plant parts, and plant seeds that are coated or at least partially coated with any of the aforementioned compositions.

EXAMPLES

The following examples are included to demonstrate certain embodiments of the invention. It will be appreciated by those of skill in the art that the techniques disclosed in the following examples represent techniques discovered by the Applicants to function well in the practice of the invention, and thus can be considered to constitute non-limiting examples for its practice. However, those of skill in the art should, in light of the instant disclosure, appreciate that many changes can be made in the specific embodiments that are disclosed, while still obtaining like or similar results, without departing from the scope of the invention.

Example 1. Culturing of PPFM Strains in a Liquid Growth Media Supplemented with a Solid Substance The liquid growth medium used to culture the PPFM cultures was a base salts medium supplemented with glycerol, peptone, and diatomaceous earth. The base salts medium used was ammonium mineral salts (AMS) medium. AMS medium contains, per liter, 700 milligrams of dibasic potassium phosphate anhydrous, 540 milligrams of monobasic potassium phosphate anhydrous, one gram of magnesium sulfate heptahydrate, 500 milligrams of ammonium chloride anhydrous, and 200 milligrams of calcium chloride dihydrate.

AMS base medium was prepared from three stock solutions, listed below:

| Stock solution I: for one liter at 50X concentration | |
|---|---|
| dibasic potassium phosphate, anhydrous | 35 grams |
| monobasic potassium phosphate, anhydrous | 27 grams |

-continued

| Stock solution II: for one liter at 50X concentration | |
|---|---|
| magnesium sulfate heptahydrate | 50 grams |
| ammonium chloride, anhydrous | 25 grams |

| Stock solution III: for one liter at 50X concentration | |
|---|---|
| calcium chloride dihydrate | 10 grams |

Stock solutions I, II, and III were autoclaved separately.

To prepare one liter of liquid AMS medium with glycerol, peptone, and diatomaceous earth, the following were added to 920 ml of distilled water:

20 ml of stock solution I
20 ml of stock solution II
20 ml of stock solution III
20 ml of a 50% glycerol stock solution
10 grams of peptone
2 grams of diatomaceous earth The resulting solution with suspended diatomaceous earth was sterilized by autoclaving.

Two liters of the above AMS medium were placed into a four-liter flask. Two milliliters of liquid culture PPFMs were added to the media to inoculate. The flask was then placed in an incubated shaker set to 240 RPM and 30 degrees Celsius. The cultures were grown for six days and then stored at 4 degrees Celsius for future use.

Example 2. Pepper Growth and Maturity Trial PPFM Water Resuspension

The PPFM strains to be tested were grown as described in Example 1 in a liquid medium supplemented with a solid substance. In the biohood, the desired amount of PPFM solution was pipetted into conical tubes (make sure to swirl/shake bottle vigorously before pipetting to suspend particulates). A centrifuge was used to spin down at 3500 RPM for 15 minutes at 23 C. While tubes were spun, a volume of tepid tap water was measured out to bring the volume of each sample up to total volume.

Liquid was carefully poured off from each tube, and the pellet was carefully kept intact. The appropriate volume of tap water was added to each tube to match its initial volume of PPFM solution. Water re-suspended PPFMS were used as quickly as possible.

Seed Preparation 100 seeds of Johnny's 'Bangkok' pepper seed (Johnny's Selected Seed, Waterville, Me., USA) were counted out per group. Soaked seeds in 30 ml tepid tap water for 30 minutes for control group. Soaked seeds in 30 ml of water resuspended PPFM strain NLS0038 for seed treated groups.

Planting

One 96-cell 1" plug tray per group was used. Two trays were filled with Farfard Super Fine Germination soilless media mix (from Sun Gro Horticulture, Agawam, Mass., USA), level with top of cell, pushed thumbs into each cell to compact, then filled again level with top of cell. Watered in well with tempered water, using the shower setting. Using tweezers, planted seeds to a depth of approximately ¼". Planted the control group first to avoid cross contamination. Placed 1 seed in each cell for a total of 96 seeds per group. Seeds were covered and lightly watered in. Labeled groups with tags and placed humidity domes on top of flats.

Growth and Development

Humidity domes was removed after germination occurred at 7 days. At 30 days maturity, 8 plants from each group were transplanted from their 96 cell trays into 4.5" green pots filled with Fafard 3B soilless media mix (from Sun Gro Horticulture, Agawam, Mass., USA). At 81 days, plants were large enough that they were falling over. All plants were of a similar size and were trimmed back several nodes to lighten plants. Control group was cut first, pruners were then sterilized and treated group was cut.

Results

At 92 days, more than half of the treated group plants displayed red ripening fruit while the control group plants exhibited no ripe fruit. Both ripe and unripe fruit were counted for all plants. Total fruit counts for the NLS0038 treated group were 15.8% higher. See Tables 2-4 below.

TABLE 2

Plants with red ripened fruit observed 92 days growth

| | +NLS0038 | Control |
|---|---|---|
| Total | 5/8 | 0/8 |

TABLE 3

Total fruit counts observed at 92 days growth

| | +NLS0038 | Control |
|---|---|---|
| | 29 | 25 |
| | 15 | 29 |
| | 30 | 31 |
| | 22 | 25 |
| | 35 | 21 |
| | 44 | 29 |
| | 46 | 32 |
| | 31 | 23 |
| Total | 252 | 215 |

TABLE 4

Total ripened fruit counts observed at 105 days growth

| | +NLS0038 | Control |
|---|---|---|
| | 15 | 20 |
| | 12 | 12 |
| | 5 | 20 |
| | 17 | 14 |
| | 14 | 9 |
| | 23 | 14 |
| | 23 | 14 |
| | 24 | 18 |
| Total | 133 | 121 |

Conclusion

Pepper plants grown to maturity from seeds treated with PPFM strain NLS0038 produced more ripened fruit and increased total fruit count from initial observations of ripening fruit at 92 days. Thirteen days after initial observations, the treated group continued to show a slight increase in ripened fruit counts.

Example 3. Seed Inoculation of 'Rex' Lettuce to Identify PPFMs that Enhance Root and Shoot Growth Seeding A 104 cell Oasis HorticubeXL™ (bottom grooved, single dibble; Smithers-Oasis North America, Kent, Ohio, USA) was placed into a 1040 flat without holes. Four cubes were removed in the center of grid to allow for bottom watering. The Oasis HorticubeXL™ was watered in so that it was fully saturated, the shower setting with tempered water was used. One seed was placed in each cell for a total of 100 seeds per group.

Inoculation of Lettuce Seeds

The PPFM strains to be tested were grown as described in Example 1 in a liquid medium supplemented with a solid substance. In the biohood, the desired amount of PPFM solution was pipetted into conical tubes (make sure to swirl/shake bottle vigorously before pipetting to suspend particulates). A centrifuge was used to spin down at 3500 RPM for 15 minutes at 23 C. While tubes were spun, a volume of tepid tap water was measured out to bring the volume of each sample up to total volume.

Liquid was carefully poured off from each tube, careful to keep the pellet intact. The appropriate volume of tap water was added to each tube to match its initial volume of PPFM solution. Water re-suspended PPFMS were used as quickly as possible.

100 microliters of solution (PPFM solution for treated groups and tap water for control groups) was pipetted onto the top of each seed. After every 3 rows, the tube was capped and shaken to resuspend any PPFMs that may have settled to the bottom. Pipette tips were changed between each group to avoid cross contamination. Tags were labeled and dated for each flat and clear humidity domes place on top of flat. The flat were placed in a growth chamber with temperature settings at 20 C and 12 hour days with 200 micromole lighting.

Growth

After five to six days, domes were removed after seeds were germinated. Flats were bottom watered only and fertilized with Jack's™ 15-16-17 (JR PETERS, Inc. Allentown, Pa., USA) at every watering (approximately every other day).

Daily repositioning of the flats was carried out to prevent potential effects on growth due to variations of light conditions in the growth chamber.

Processing

Flats were harvested between two and three weeks. Clear humidity domes were placed on each flat to prevent evapotranspiration during transport. Domes were left in place until flat was being processed. Each plant was cut directly below the cotyledons and immediately weighed on an analytical balance.

Observations

It was observed that some strains repeatedly showed an increase in shoot biomass of Lettuce seedlings when a seed was treated at the time of planting. Visual observations of root mass and development were also made, treated groups showed more growth at the time of harvest. Due to the natural variance of biological systems all samples sizes were 98-100 plants minimum and anything below 12% difference was not considered significant.

Conclusion

It was apparent that strains NLS0017, NLS0020, NLS0066, NLS0065, and NLS0089 show an increase in wet weight of lettuce seedlings following seed treatment. Strains NLS0069, NLS0037, NLS0038, and NLS0062 exhibited negligible increases in wet weight in comparison to the controls. Also noted along with an increase in shoot biomass is a corresponding increase in root development.

TABLE 5

Effects of seed treatments on lettuce growth

| strain | titer | control | seedling wet weight (mg) experimental | difference (%) | confidence interval |
|---|---|---|---|---|---|
| NLS0017 | 2.7E+08 | 226.18 | 306.36 | 35.45% | 0.000 |
| NLS0017 | 1.4E+08 | 298.27 | 353.34 | 18.46% | 0.012 |
| NLS0017 | 2.7E+08 | 169.56 | 176.68 | 4.20% | 0.567 |
| NLS0017 | 1.1E+09 | 98.92 | 167.51 | 69.34% | 0.000 |
| NLS0020 | 7.2E+08 | 226.18 | 274.46 | 21.35% | 0.027 |
| NLS0020 | 1.2E+09 | 98.92 | 157.11 | 58.83% | 0.000 |
| NLS0020 | 1.2E+09 | 462.20 | 614.72 | 33.00% | 0.000 |
| NLS0021 |  | 462.20 | 539.39 | 16.70% | 0.008 |
| NLS0037 | 3.0E+08 | 226.18 | 258.68 | 14.37% | 0.085 |
| NLS0038 | 5.2E+07 | 462.20 | 514.99 | 11.42% | 0.070 |
| NLS0042 | 2.1E+08 | 226.18 | 310.85 | 37.44% | 0.000 |
| NLS0042 | 1.1E+08 | 169.56 | 189.46 | 11.73% | 0.105 |
| NLS0046 | 1.8E+09 | 462.20 | 511.78 | 10.73% | 0.084 |
| NLS0062 | 1.8E+08 | 169.56 | 187.62 | 10.65% | 0.121 |
| NLS0064 |  | 169.56 | 157.67 | −7.01% | 0.275 |
| NLS0065 | 1.2E+08 | 169.56 | 211.92 | 24.98% | 0.001 |
| NLS0065 | 9.1E+07 | 98.92 | 132.35 | 33.80% | 0.000 |
| NLS0066 | 5.9E+08 | 56.15 | 69.57 | 23.91% | 0.000 |
| NLS0066 | 4.2E+08 | 546.61 | 665.46 | 21.74% | 0.000 |
| NLS0066 | 1.2E+08 | 98.92 | 129.81 | 31.23% | 0.000 |
| NLS0068 | 3.1E+08 | 213.52 | 234.95 | 10.04% | 0.029 |
| NLS0069 | 5.6E+07 | 226.18 | 244.25 | 7.99% | 0.307 |
| NLS0069 | 5.6E+07 | 298.27 | 332.53 | 11.49% | 0.144 |
| NLS0089 | 1.5E+08 | 98.92 | 146.99 | 48.60% | 0.000 |
| NLS0089 |  | 462.20 | 600.82 | 29.99% | 0.000 |

[1]Each line represents data obtained from a separate flats of plants obtained from treated seed versus control seed.

Example 4. Foliar Application of 'Rex' Lettuce to Identify PPFMs that Enhance Root and Shoot Growth Seeding A 104 cell Oasis HorticubeXL (bottom grooved, single dibble) was placed into a 1020 flat without holes. Four cubes were removed in the center of grid to allow for bottom watering. Oasis was watered in so that it was fully saturated, the shower setting with tempered water was used. One seed was placed in each cell for a total of 100 seeds per group. Tags were labeled and dated for each flat and clear humidity domes place on top of flat. The flat were placed in a growth chamber with temperature settings at 20 C and 12-hour days with 200 micromole lighting.

Inoculation of Lettuce seedlings

After five to six days, domes were removed after seeds had germinated. Plants were inoculated at this time, when only the cotyledons had emerged. The PPFM strains to be tested were grown as described in Example 1 in a liquid medium supplemented with a solid substance. The PPFM strains to be tested were grown as described in Example 1 in a liquid medium supplemented with a solid substance. In the biohood, the desired amount of PPFM solution was pipetted into conical tubes (after swirling/shaking the solution vigorously before pipetting to suspend particulates). A centrifuge was used to spin down at 3500 RPM for 15 minutes at 23 C. While tubes were spun, a volume of tepid tap water was measured out to bring the volume of each sample up to total volume.

Liquid was carefully poured off from each tube, careful to keep the pellet intact. The appropriate volume of tap water was added to each tube to match its initial volume of PPFM solution. Water re-suspended PPFMS were used as quickly as possible.

100 mL of PPFM solution (tap water for control) was poured into a 1 L Solo™ Handheld Sprayer (Solo™, Newport News, Va., USA). The flat was removed from the group to avoid cross contamination. The finest mist setting was used and an even coat of solution was sprayed over the top of the seedlings, ensuring even coverage across the entire flat. For each group this was repeated, using appropriate treatment.

Growth

Flats were bottom watered only and fertilized with Jack's™ 15-16-17 (JR PETERS, Inc. Allentown, Pa., USA) at every watering (approximately every other day). Daily repositioning of the flats was carried out to prevent potential effects on growth due to variations of light conditions in the growth chamber.

Processing

Flats were harvested between two and three weeks. Clear humidity domes were placed on each flat to prevent evapotranspiration during transport. Domes were left in place until flat was being processed. Each plant was cut directly below the cotyledons and immediately weighed on an analytical balance.

Observations

It was been observed that some strains repeatedly show an increase in shoot biomass of Lettuce seedlings when the seedling was treated at the cotyledon stage. Visual observations of root mass and development were also made, that treated groups showed more growth at the time of harvest. Due to the natural variance of biological systems all samples sizes were a 98-100 plants minimum and anything below 12% difference was not considered significant.

Conclusion

It is apparent that strains NLS0042, NLS0017, NLS0020, and NLS0068 show an increase in wet weight of lettuce seedlings following foliar application. Strains NLS0069, NLS0037, NLS0038, and NLS0062 exhibited negligible increases in wet weight in comparison to the controls. Also noted along with an increase in shoot biomass is a corresponding increase in root development.

TABLE 6

Effects of foliar treatments on lettuce growth

| strain | titers | seedling wet weight (mg) control | seedling wet weight (mg) experimental | difference (%) | confidence interval |
|---|---|---|---|---|---|
| NLS0017 | 1.4E+08 | 197.04 | 213.76 | 8.49% | 0.075 |
| NLS0017 | 1.1E+09 | 157.72 | 211.03 | 33.81% | 0.000 |
| NLS0020 | 2.2E+08 | 104.41 | 145.95 | 39.79% | 0.000 |
| NLS0020 | 7.2E+08 | 205.34 | 247.12 | 20.34% | 0.030 |
| NLS0020 | 1.2E+09 | 280.84 | 260.95 | −7.08% | 0.224 |
| NLS0021 | 1.6E+07 | 157.72 | 178.46 | 13.15% | 0.021 |
| NLS0037 |  | 197.04 | 198.93 | 0.96% | 0.846 |
| NLS0038 | 7.4E+07 | 197.04 | 186.04 | −5.58% | 0.250 |
| NLS0042 | 9.3E+07 | 103.36 | 127.05 | 22.92% | 0.000 |
| NLS0042 | 2.1E+08 | 205.34 | 235.92 | 14.89% | 0.095 |
| NLS0042 | 6.4E+07 | 298.27 | 331.62 | 11.18% | 0.138 |
| NLS0042 | 1.1E+08 | 157.72 | 196.12 | 24.35% | 0.000 |
| NLS0046 | 1.8E+09 | 157.72 | 195.03 | 23.66% | 0.000 |
| NLS0062 |  | 280.84 | 243.09 | −13.44% | 0.018 |
| NLS0064 |  | 205.34 | 240.47 | 17.10% | 0.042 |
| NLS0064 |  | 298.27 | 306.88 | 2.89% | 0.691 |
| NLS0065 | 4.2E+08 | 197.04 | 214.59 | 8.91% | 0.077 |
| NLS0066 | 5.9E+08 | 205.34 | 241.92 | 17.81% | 0.035 |
| NLS0066 | 1.2E+08 | 280.84 | 166.98 | −40.54% | 0.000 |
| NLS0068 | 1.7E+08 | 104.41 | 204.26 | 95.65% | 0.000 |
| NLS0068 | 1.6E+08 | 205.34 | 288.46 | 40.47% | 0.000 |
| NLS0068 | 3.1E+08 | 298.27 | 296.68 | −0.53% | 0.944 |
| NLS0068 | 3.1E+08 | 280.84 | 264.65 | −5.76% | 0.337 |
| NLS0068 | 3.1E+08 | 157.72 | 183.84 | 16.56% | 0.010 |

TABLE 6-continued

Effects of foliar treatments on lettuce growth

| strain | titers | seedling wet weight (mg) control | seedling wet weight (mg) experimental | difference (%) | confidence interval |
|---|---|---|---|---|---|
| NLS0069 | 4.5E+07 | 99.85 | 103.54 | 3.70% | 0.711 |
| NLS0089 | 1.3E+09 | 280.84 | 282.94 | 0.75% | 0.896 |

[1]Each line represents data obtained from separate flats of treated versus control plants.

Example 5. Additional Pepper Growth and Maturity Trial

Pepper plants were subjected to additional trials essentially as described in Example 2 except that *Methylobacterium* strains NLS0037, NLS0042, and NLS0062 were tested. The results are presented in Table 7.

TABLE 7

Effects of foliar treatment on flower and pepper count

| Treatment | Flower count (average per plant) 46 days post-planting | Pepper count (average per plant) 64 days post-planting |
|---|---|---|
| Untreated | 18.3 | 25.4 |
| NLS0037 | 24.8 (p = 0.08) | 40.8 (p < 0.05) |
| NLS0042 | 25.1 (p = 0.09) | 38.9 (p < 0.05) |
| NLS0062 | 24.1 (p = 0.06) | 38.8 (p = 0.06) |

It was clear from these experiments that the indicated *Methylobacterium* treatments had a positive effect on both flower and pepper counts.

REFERENCES

1. Abanda-Nkpwatt, D., M. Musch, J. Tschiersch, M. Boettner, and W. Schwab. 2006. Molecular interaction between *Methylobacterium extorquens* and seedlings: growth promotion, methanol consumption, and localization of the methanol emission site. J. Exp. Bot. 57: 4025-4032.
2. Broekaert W F, Terras F R, Cammue B P, Vanderleyden J (1990) An automated quantitative assay for fungal growth inhibition. FEMS Microbiology Letters 69: 55-60.
3. Cao, Y-R, Wang, Q., Jin, R-X., Tang, S-K., He, W-X., Lai, H-X, Xu, L-H., and C-L Jiang. 2011. *Methylobacterium soli* sp. nov. a methanol-utilizing bacterium isolated from the forest soil. Antonie van Leeuwenhoek (2011) 99:629-634.
4. Corpe, W. A., and D. V. Basile. 1982. Methanol-utilizing bacteria associated with green plants. Devel. Industr. Microbiol. 23: 483-493.
5. Corpe, W. A., and S. Rheem. 1989. Ecology of the methylotrophic bacteria on living leaf surfaces. FEMS Microbiol. Ecol. 62: 243-250.
6. Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.
7. Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.

8. Holland, M. A. 1997. *Methylobacterium* and plants. Recent. Res. Devel. in Plant Physiol. 1: 207-213.
9. Holland, M. A., and J. C. Polacco. 1994. PPFMs and other covert contaminants: Is there more to plant physiology than just plant? Annu Rev. Plant Physiol. Plant Mol. Biol. 45: 197-209.
10. Kutschera, U. 2007. Plant-associated methylobacteria as co-evolved phytosymbionts. A hypothesis. Plant Signal Behav. 2: 74-78.
11. Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.
12. Madhaiyan, M., S. Poonguzhali, H. S. Lee, K. Hari, S. P. Sundaram, and T. M. Sa. 2005. Pink-pigmented facultative methylotrophic bacteria accelerate germination, growth and yield of sugarcane clone Co86032 (*Saccharum officinarum* L.) Biol. Fertil. Soils 41: 350-358.
13. Madhaiyan, M., S. Poonguzhali, M. Senthilkumar, S. Seshadri, H. Chung, J. Yang, S. Sundaram, and T. Sa. 2004. Growth promotion and induction of systemic resistance in rice cultivar C0-47 (*Oryza sativa* L.) by *Methylobacterium* spp. Bot. Bull. Acad. Sin. 45: 315-324.
14. Madhaiyan, M., S. Poonguzhali, and T. Sa. 2007. Influence of plant species and environmental conditions on epiphytic and endophytic pink-pigmented facultative methylotrophic bacterial populations associated with field-grown rice cultivars. J Microbiol Biotechnol. 2007 October; 17(10): 1645-54.
15. Stanier, R. Y., N. J. Palleroni, and M. Doudoroff. 1966. The aerobic pseudomonads: A taxonomic study. J. Gen. Microbiol. 43: 159-271.
16. Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220,
17. Sy, A., A. C. J. Timmers, C. Knief, and J. A. Vorholt. 2005. Methylotrophic metabolism is advantageous for *Methylobacterium extorquens* during colonization of *Medicago truncatula* under competitive conditions. Appl. Environ. Microbiol. 71: 7245-7252.
18. Vogel, H. J., and D. M. Bonner. 1956. Acetylornithinase of *Escherichia coli*: Partial purification and some properties. J. Biol. Chem. 218: 97-106.
19. Vogel, H. J. 1956. A convenient growth medium for *Neurospora* (Medium N). Microbial Genet Bull 13: 42-43
20. Whittenbury, R., S. L. Davies, and J. F. Wilkinson. 1970. Enrichment, isolation and some properties of methane-utilizing bacteria. J. Gen. Microbiol. 61: 205-218.

The inclusion of various references herein is not to be construed as any admission by the Applicants that the references constitute prior art. Applicants expressly reserve their right to challenge any allegations of unpatentability of inventions disclosed herein over the references included herein.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for improving fruit production, said method comprising:
   (a) applying a composition comprising *Methylobacterium* and an agriculturally acceptable adjuvant, excipient, or combination thereof to a fruit bearing plant, wherein said *Methylobacterium* is NLS0037 (NRRL B-50941), NLS0038 (NRRL B-50942), NLS0042 (NRRL B-50932), NLS0062 (NRRL B-50937), and wherein said fruit bearing plant is an apple, pear, grape, citrus, melon, pepper, berry, kiwi, mango, or banana plant, and,
   (b) harvesting fruit from said plant, wherein said plant exhibits faster fruit set, increased fruit set, earlier fruit maturation, and/or more uniform fruit maturation compared to an untreated control plant, thereby obtaining improved fruit production.

2. The method of claim 1, wherein said fruit bearing plant is a pepper plant.

3. The method of claim 1, wherein said composition is depleted of substances that promote growth of resident microorganisms on said plant or seed.

4. The method of claim 1, wherein the *Methylobacterium* is NLS0062 (NRRL B-50937).

5. The method of claim 4, wherein the *Methylobacterium* is NLS0037 (NRRL B-50941) or NLS0038 (NRRL B-50942).

6. The method of claim 1, wherein said composition coats or partially coats said plant or a part thereof.

7. A method for improving fruit production, said method comprising:
   (a) applying a composition comprising *Methylobacterium* to a seed of a fruit bearing plant wherein said *Methylobacterium* sp. is NLS0037 (NRRL B-50941), NLS0038 (NRRL B-50942), NLS0042 (NRRL B-50932), NLS0062 (NRRL B-50937), and an agriculturally acceptable adjuvant, excipient, or combination thereof and wherein said fruit bearing plant is an apple, pear, grape, citrus, melon, pepper, berry, kiwi, mango, or banana plant; and,
   (b) harvesting fruit from a plant grown from said seed, wherein said plant grown from said seed exhibits faster fruit set, increased fruit set, earlier fruit maturation, and/or more uniform fruit maturation compared to an untreated control plant, thereby obtaining improved fruit production.

8. The method of claim 7, wherein said composition comprises the *Methylobacterium* at a titer of about $1 \times 10^6$ colony-forming units per gram (CFU/gm) of solid to about $1 \times 10^{14}$ CFU/gm of solid for a composition comprising a solid substance with adherent *Methylobacterium* grown thereon or at a titer of about $1 \times 10^6$ CFU/mL to about $1 \times 10^{11}$ CFU/mL for a composition comprising an emulsion having the *Methylobacterium* grown therein.

9. The method of claim 7, wherein said fruit bearing plant is a pepper plant.

10. The method of claim 7, wherein the *Methylobacterium* is NLS0037 (NRRL B-50941) or NLS0038 (NRRL B-50942).

11. The method of claim 7, wherein the *Methylobacterium* is NLS0042 (NRRL B-50932), NLS0062 (NRRL B-50937).

12. The method of claim 7, wherein said composition coats or partially coats said seed.

13. A method of treating a fruit bearing plant or seed with a composition comprising *Methylobacterium*, said method comprising:
(a) obtaining a *Methylobacterium* preparation comprising a solid substance with the *Methylobacterium* grown thereon with a *Methylobacterium* titer of $1\times10^6$ colony-forming units per gram (CFU/gm) of solid to about $1\times10^{14}$ CFU/gm of solid or an emulsion with *Methylobacterium* grown therein at a titer of about $1\times10^6$ CFU/mL to about $1\times10^{11}$ CFU/mL, wherein said *Methylobacterium* is NLS0037 (NRRL B-50941), NLS0038 (NRRL B-50942), NLS0042 (NRRL B-50932), NLS0062 (NRRL B-50937); and
(b) applying said composition to a plant, a part thereof, or a seed, wherein said plant, part thereof, or seed is an apple, pear, grape, citrus, melon, pepper, berry, kiwi, mango, or banana plant, part thereof, or seed and wherein said plant or plant grown from said seed exhibits faster fruit set, increased fruit set, earlier fruit maturation, and/or more uniform fruit maturation compared to an untreated control plant, thereby obtaining improved fruit production.

14. The method of claim 1, wherein the *Methylobacterium* in said composition are provided as a solid substance with adherent *Methylobacterium* grown thereon or as an emulsion having the *Methylobacterium* grown therein.

15. The method of claim 14, wherein said composition comprises *Methylobacterium* at a titer of about $1\times10^6$ colony-forming units per gram (CFU/gm) of solid to about $1\times10^{14}$ CFU/gm of solid for the solid-containing composition or at a titer of about $1\times10^6$ CFU/mL to about $1\times10^{11}$ CFU/mL for the emulsion-containing composition.

16. The method of claim 14, wherein the solid substance with the adherent *Methylobacterium* grown thereon is provided in a liquid or an emulsion.

* * * * *